United States Patent [19]

Hill et al.

[11] Patent Number: 4,493,326
[45] Date of Patent: Jan. 15, 1985

[54] AUTOMATIC BLOOD PRESSURE SYSTEM WITH SERVO CONTROLLED INFLATION AND DEFLATION

[75] Inventors: Jeremy R. Hill, Weston; Donald Malinouskas, Monroe, both of Conn.

[73] Assignee: United States Surgical Corporation, Norwalk, Conn.

[21] Appl. No.: 344,051

[22] Filed: Jan. 29, 1982

Related U.S. Application Data

[62] Division of Ser. No. 81,551, Oct. 3, 1979, Pat. No. 4,328,810.

[51] Int. Cl.³ .................................................. A61B 5/02
[52] U.S. Cl. ...................................... 128/680; 128/682
[58] Field of Search ............................... 128/680-682, 128/686; 364/415-417

[56] References Cited

U.S. PATENT DOCUMENTS

| | | | |
|---|---|---|---|
| 3,905,353 | 9/1975 | Lichowsky . | |
| 3,905,354 | 9/1975 | Lichowski | 128/681 |
| 4,058,117 | 11/1977 | Kaspari et al. . | |
| 4,069,815 | 1/1978 | Lee | 128/683 |
| 4,116,230 | 9/1978 | Gorelick | 128/682 |
| 4,146,018 | 3/1979 | Aldridge et al. . | |
| 4,216,779 | 8/1980 | Squires | 128/682 |
| 4,262,675 | 4/1981 | Kubo | 128/680 |
| 4,313,445 | 2/1982 | Georgi . | |
| 4,378,807 | 4/1983 | Peterson et al. | 128/682 |

FOREIGN PATENT DOCUMENTS

| | | |
|---|---|---|
| 2758895 | 8/1978 | Fed. Rep. of Germany . |
| 2811362 | 11/1978 | Fed. Rep. of Germany . |
| 2843113 | 4/1979 | Fed. Rep. of Germany . |
| 2846530 | 6/1979 | Fed. Rep. of Germany . |
| 792875 | 4/1958 | United Kingdom . |
| 1460412 | 1/1977 | United Kingdom . |
| 1460413 | 1/1977 | United Kingdom . |
| 2023849A | 9/1979 | United Kingdom . |

Primary Examiner—Kylel Howell
Assistant Examiner—Francis J. Jaworski
Attorney, Agent, or Firm—A. Peter Adler; John E. Nathan; Robert R. Jackson

[57] ABSTRACT

A blood pressure system which cycles through an inflation cycle and a deflation cycle during which systolic and diastolic blood pressure in a patient is automatically measured. The blood pressure system basically comprises an inflatable pressure cuff system for accomplishing occlusion and the subsequent opening of an artery in a patient being monitored, and an electrical system for increasing and decreasing the pressure in the cuff under servo loop control and for displaying the systolic and diastolic measurements. A pressure transducer produces an electrical signal indicative of the actual pressure in the cuff. A solenoid valve permits selective pressure decrease during the deflation cycle. A rotary vane compression pump provides pressure increase during the inflation cycle. During the inflation cycle, pressure increase in the cuff is accomplished by a servo control loop comprising the transducer, the pump, and an inflate/deflate controller. During the deflation cycle, pressure decrease in the cuff is accomplished by a servo control loop comprising the transducer, the controller, and the solenoid valve. In both the inflation cycle and the deflation cycle, the controller receives the signal from the transducer and produces an error signal indicative of the difference between the actual rate of change of pressure in the cuff and a desired rate of change of pressure. Additional circuitry in the controller variably duty cycle modulates the error signal to produce a control signal. In the inflation cycle, the control signal actuates the pump to increase the pressure. In the deflation cycle, the control signal actuates the solenoid valve to decrease the pressure.

7 Claims, 48 Drawing Figures

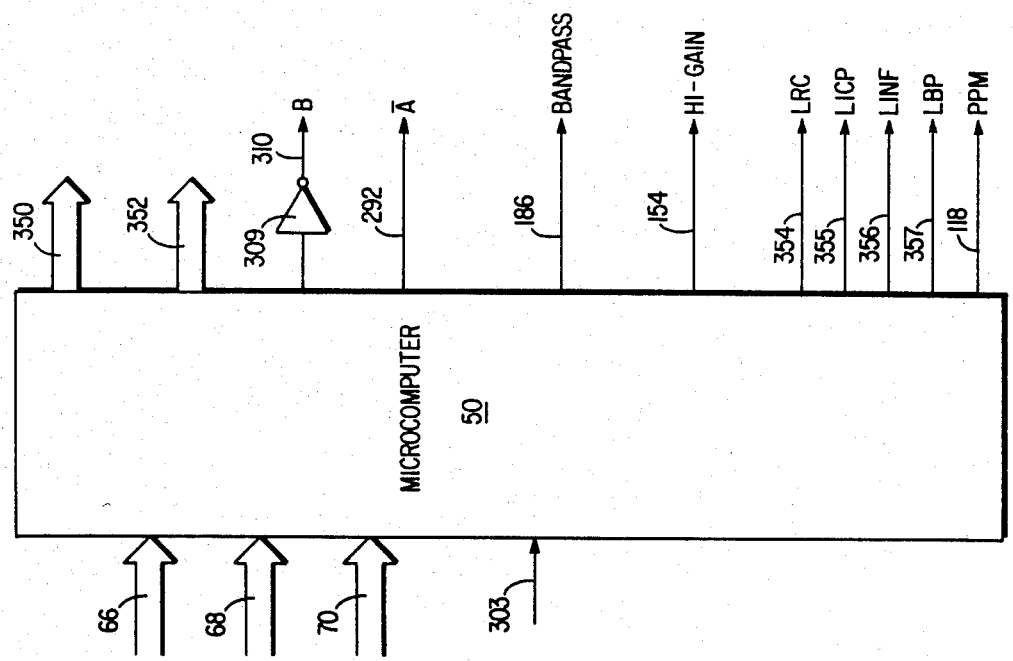
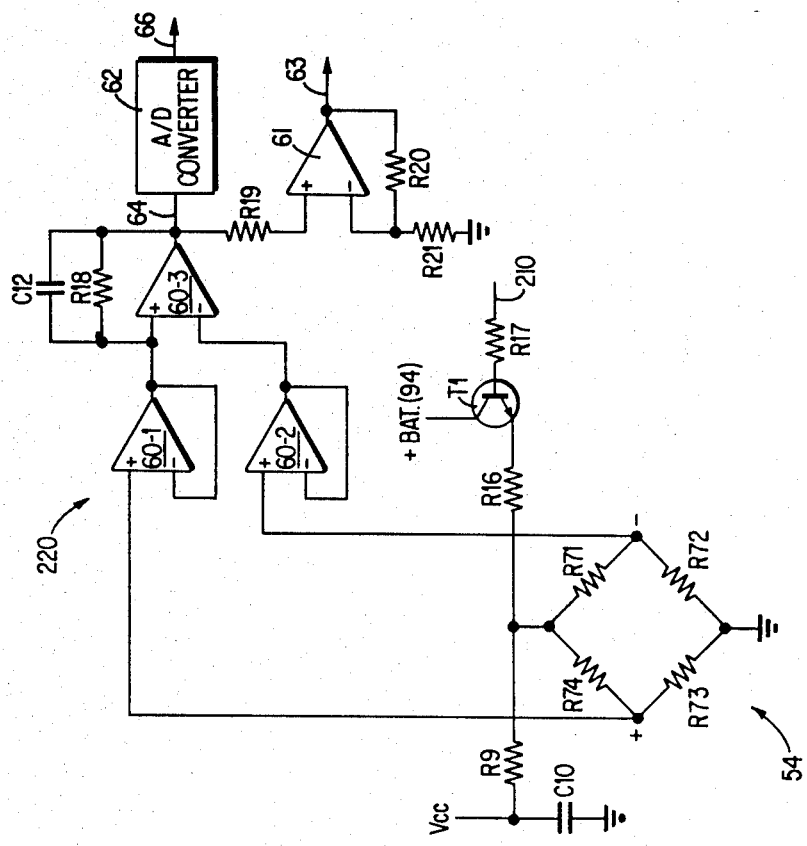

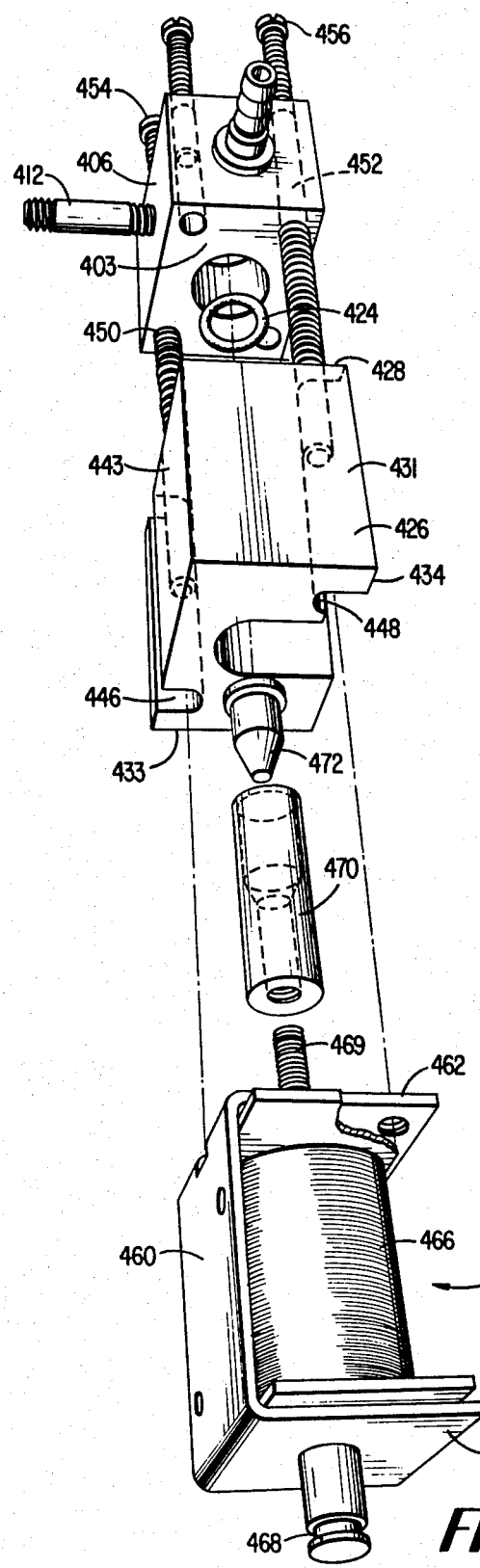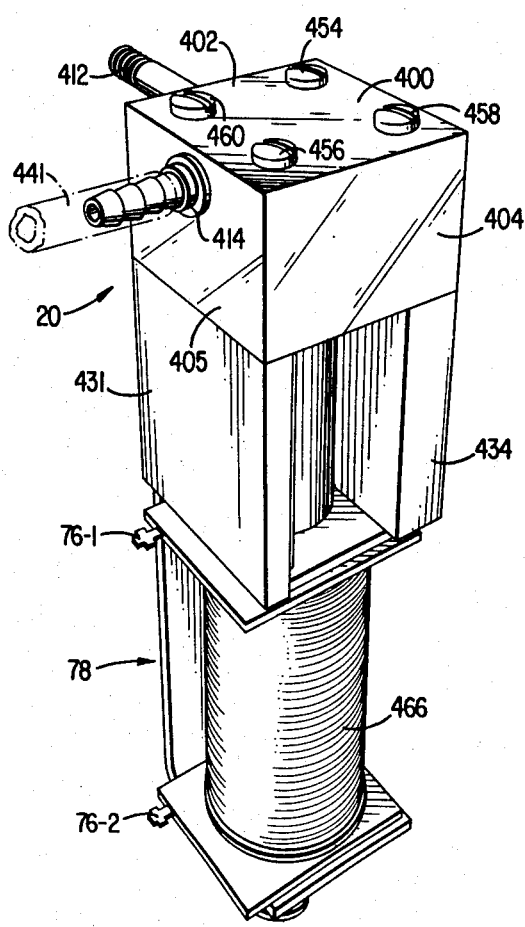
FIG. 12
FIG. 13

FIG. 21
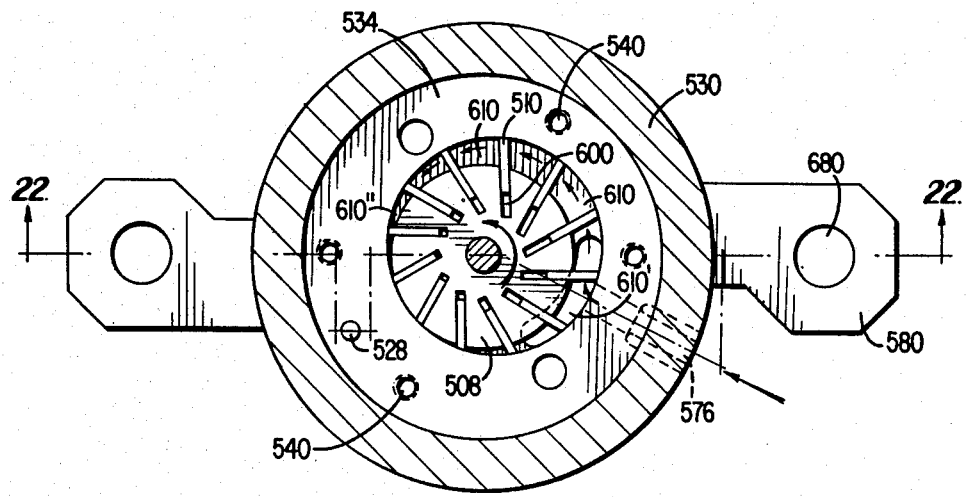
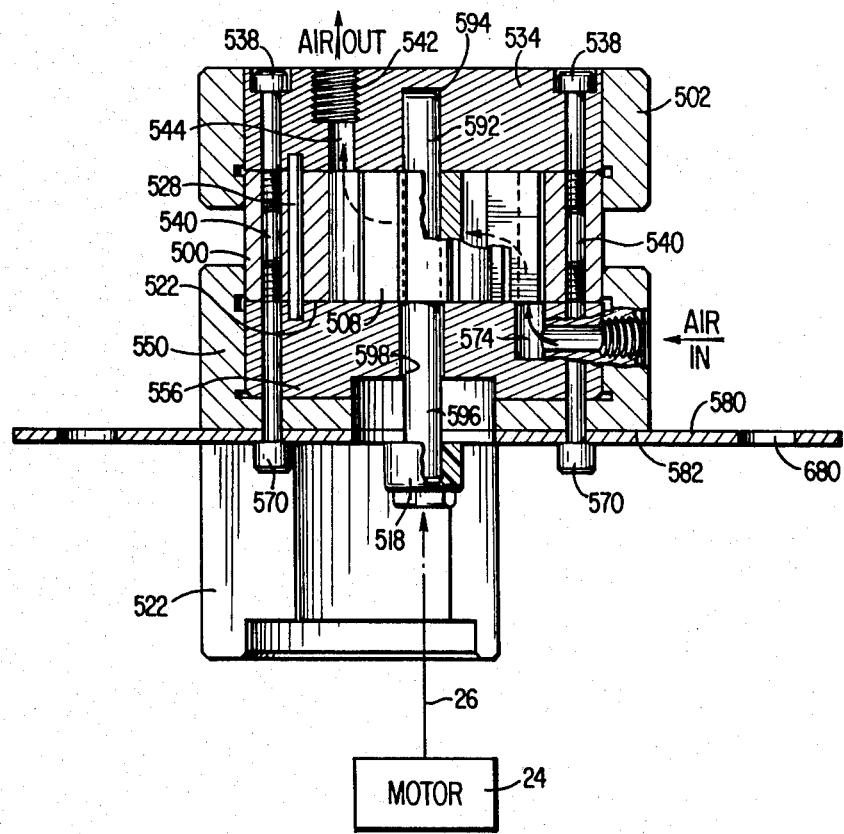
FIG. 22

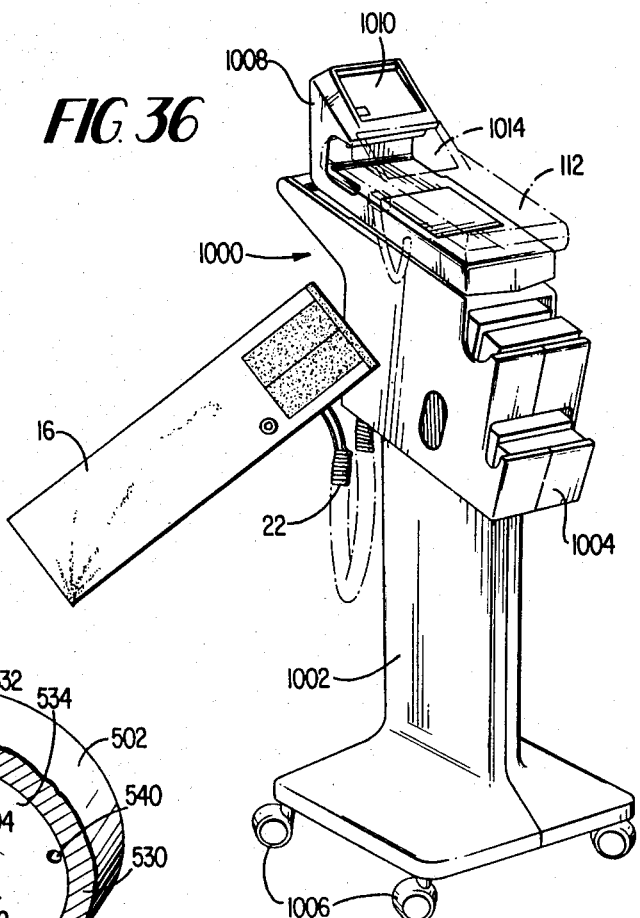
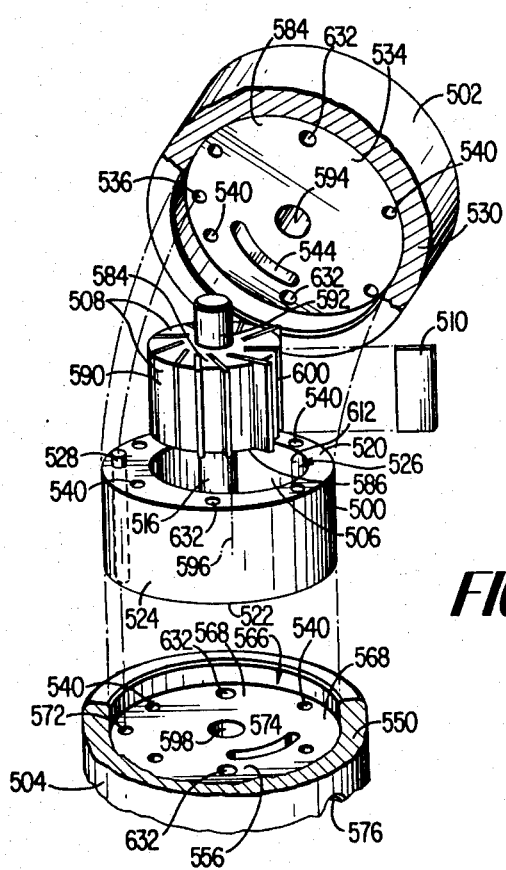
FIG. 36
FIG. 24

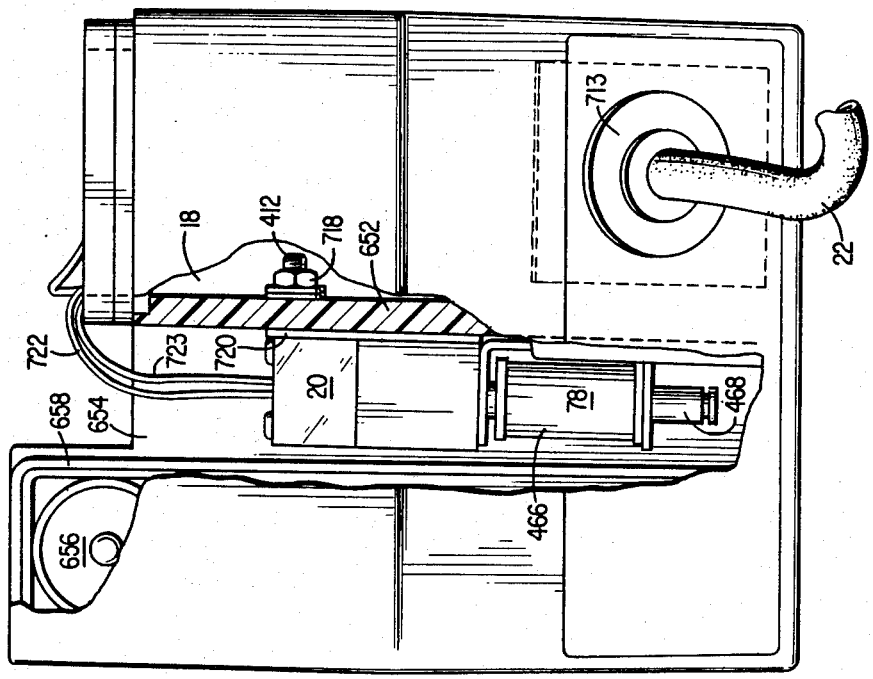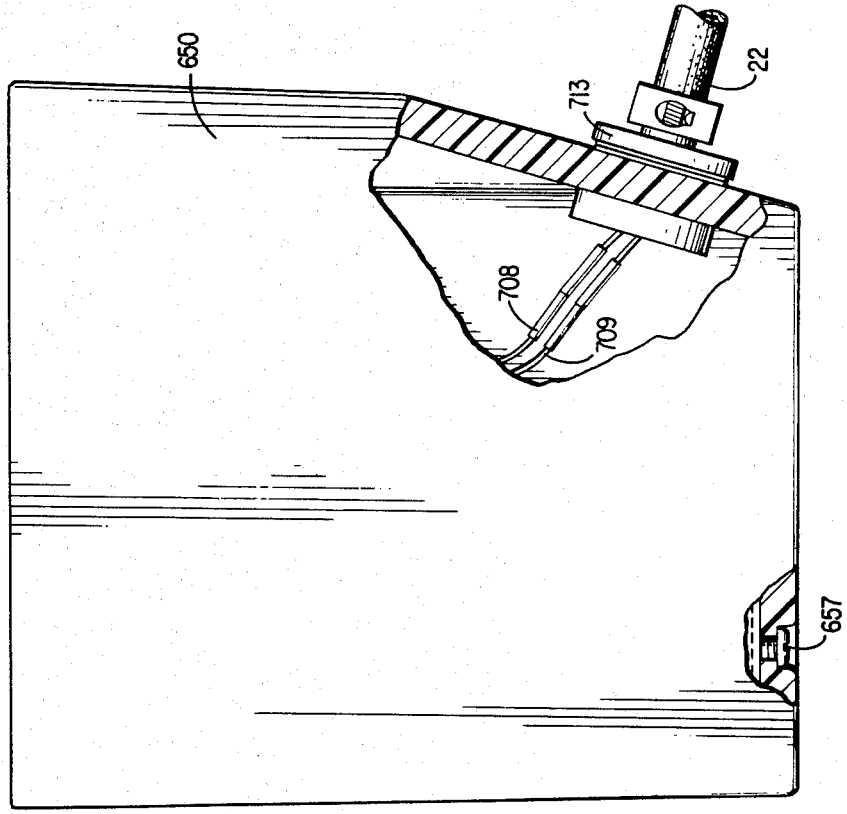

TO FIG. 43B

AUTOMATIC BLOOD PRESSURE SYSTEM WITH SERVO CONTROLLED INFLATION AND DEFLATION

This is a divisional of application Ser. No. 81,551 filed Oct. 3, 1979, and now U.S. Pat. No. 4,328,810.

BACKGROUND OF THE INVENTION

1. Field of the Invention

This invention relates to a system for automatically measuring and monitoring systolic and diastolic blood pressure in the human body by employing non-invasive techniques.

2. Description of the Prior Art

The standard clinical method for the non-invasive measurement of blood pressure employs a device called a sphygmomanometer which comprises an inflatable cuff connected to a manometer tube in which the height of a column of mercury indicates the pressure in the cuff. The cuff is wrapped around a limb, usually the upper arm, and inflated until the pulse in the artery of the limb is suppressed because the artery is squeezed shut. The cuff is then gradually deflated, so that blood begins to flow through the artery again. The turbulent flow of the blood within the artery causes a characteristic sound known as a Korotkoff sound of K-sound. The pressure indicated by the manometer at that instant corresponds to the systolic blood pressure. With further deflation of the cuff, the turbulent flow in the now fully opened artery becomes so-called "laminar flow" and the sound ceases. The pressure measured at that instant corresponds to the diastolic blood pressure.

There are any number of prior art devices which have automated the procedure described above. Typically, these blood pressure measuring systems consist of a microphone for sensing Korotkoff sounds, a cuff pressurization source, electronic circuitry for processing Korotkoff sounds, and a technique for displaying systolic and diastolic blood pressure values.

Typically, an automated blood pressure instrument is preset during manufacture to inflate to a maximum cuff pressure that is above the maximum expected pressure. In this case, the applied pressure is determined by the patient with the highest expected pressure. Some machines have the ability to remember previous pressure readings from the same patient. In these machines, the problem of maximum cuff pressure is reduced when the instrument is dedicated to successive measurements even through "first readings" must often be disregarded. Other machines inflate to a typical maximum value; if shown to be inadequate, they will then modify the inflation cycle to automatically re-inflate to a higher pressure.

SUMMARY OF THE INVENTION

The present invention relates to a blood pressure system which cycles through an inflation cycle and a deflation cycle during which systolic and diastolic pressure in a patient is automatically measured. The blood pressure system basically comprises a pressure cuff system for accomplishing occlusion and the subsequent opening of an artery in a patient being monitored, and an electrical system for controlling the pressure cuff system and for displaying the systolic and diastolic measurements.

A blood pressure cuff, which is adapted for use about a limb of the patient, is capable of being inflated to occlude the artery of the limb. The blood pressure cuff contains an inflatable bladder which is in fluid communication with a pressure chamber by way of a flexible tubing. The communication between the pressure chamber and the blood pressure cuff is such that, at any given time, the pressure within the chamber is substantially the same as the pressure within the cuff.

A pressure transducer is in fluid communication with the pressure chamber by way of a solenoid valve. The pressure transducer produces an electrical signal indicative of the actual pressure within the chamber. The solenoid valve is used to selectively bleed the pressure chamber during the deflation cycle.

An inflate/deflate controller receives the signal from the pressure transducer and produces an error signal indicative of the difference between the actual rate of change of pressure within the chamber and the desired rate of change of pressure within the chamber. During the inflation mode of the blood pressure system, the inflate/deflate controller contains circuitry for duty cycle modulating the error signal to produce a control signal which acts upon a motor-pump combination, contained within the pressure chamber, to increase the pressure within the chamber and thereby inflate the cuff. The pump is a rotary vane compression pump which relies upon the outside atmosphere as a source of air.

During the deflation cycle, the inflate/deflate controller contains circuitry for duty cycle modulating the error signal to produce a second control signal to activate a solenoid contained in the solenoid valve to selectively decrease the pressure within the chamber, thereby deflating the cuff.

In order to automatically carry out the inflation and deflation cycle of the blood pressure system, a dedicated controller is employed. A microphone, contained within the blood pressure cuff, and positioned near the artery to be occluded, produces an electrical signal indicative of pulsatile activity within the artery. A K-sound detector receives the signal and relays the information to the dedicated controller. In the blood pressure system of the subject invention, K-sound detection continually takes place during both the inflation and deflation cycles of the instrument. The dedicated controller is configured so as to provide control signals to the inflate/deflate controller to carry out appropriately the inflation and deflation cycles.

As part of the blood pressure instrument, there is also provided a pulse transfer system for receiving and processing information from the dedicated controller in order to produce a display of heart rate in beats per minute. Basically, the pulse transfer system employs a separate unit which is normally usable apart from the blood pressure system for measuring temperature, pressure and respiration. The transfer of heart rate information between the blood pressure system and the separate unit is by way of inductive coupling.

It is an object of the present invention to provide a self-contained automatic blood pressure measuring system.

It is another object of the present invention to provide a blood pressure measuring system which automatically cycles through an inflation cycle and a deflation cycle during which systolic and diastolic blood pressure values are measured and displayed.

It is a further object of the present invention to provide a blood pressure measuring system in which K- sounds are continuously monitored during both the inflation cycle and deflation cycle of the system.

It is yet an object of the present invention to provide a blood pressure measuring system which may be used in conjunction with a physiological parameter measuring device for display of heart pulse rate, while also measuring blood pressure.

It is yet an object of the present invention to provide an automatic blood pressure measuring system which measures systolic and diastolic blood pressures by noninvasive means.

It is still another object of the present invention to provide a blood pressure measuring system that employs a solenoid valve assembly, which is used to deflate the blood pressure cuff.

It is yet further object of the present invention to provide a blood pressure system which employs a pressure chamber and a compression pump to inflate the blood pressure cuff.

It is still a further object of the present invention to provide a blood pressure system which transfers information by inductive coupling to a physiological parameter measuring device for display of pulse information.

These and other objects will become apparent from the following drawings and detailed description.

BRIEF DESCRIPTION OF THE DRAWINGS

FIG. 3 is a schematic diagram showing embodiments of a pressure sensor and a signal converter for use in the embodiment shown in FIG. 1.

FIG. 5 is a schematic diagram showing the various inputs and outputs of the dedicated controller shown in FIG. 1.

FIG. 12 is an exploded view of the solenoid valve assembly.

FIG. 13 is a perspective view of the solenoid valve assembly shown in FIG. 12.

FIG. 21 is a secitonal view taken along lines 21—21 of FIG. 19.

FIG. 22 is a sectional view taken along lines 22—22 of FIG. 21.

FIG. 24 is an exploded view of the pump with portions removed.

FIG. 30 is a side plan view, partially cut away, of the pump housing with the blood pressure cuff hose mounted.

FIG. 31 is a side plan view of the pump housing partially cut away to reveal the mounting of the solenoid valve assembly and the battery.

FIG. 36 is a perspective view of an embodiment of the housing for the blood pressure system.

DETAILED DESCRIPTION OF THE DRAWINGS

Introduction

Figure 1:
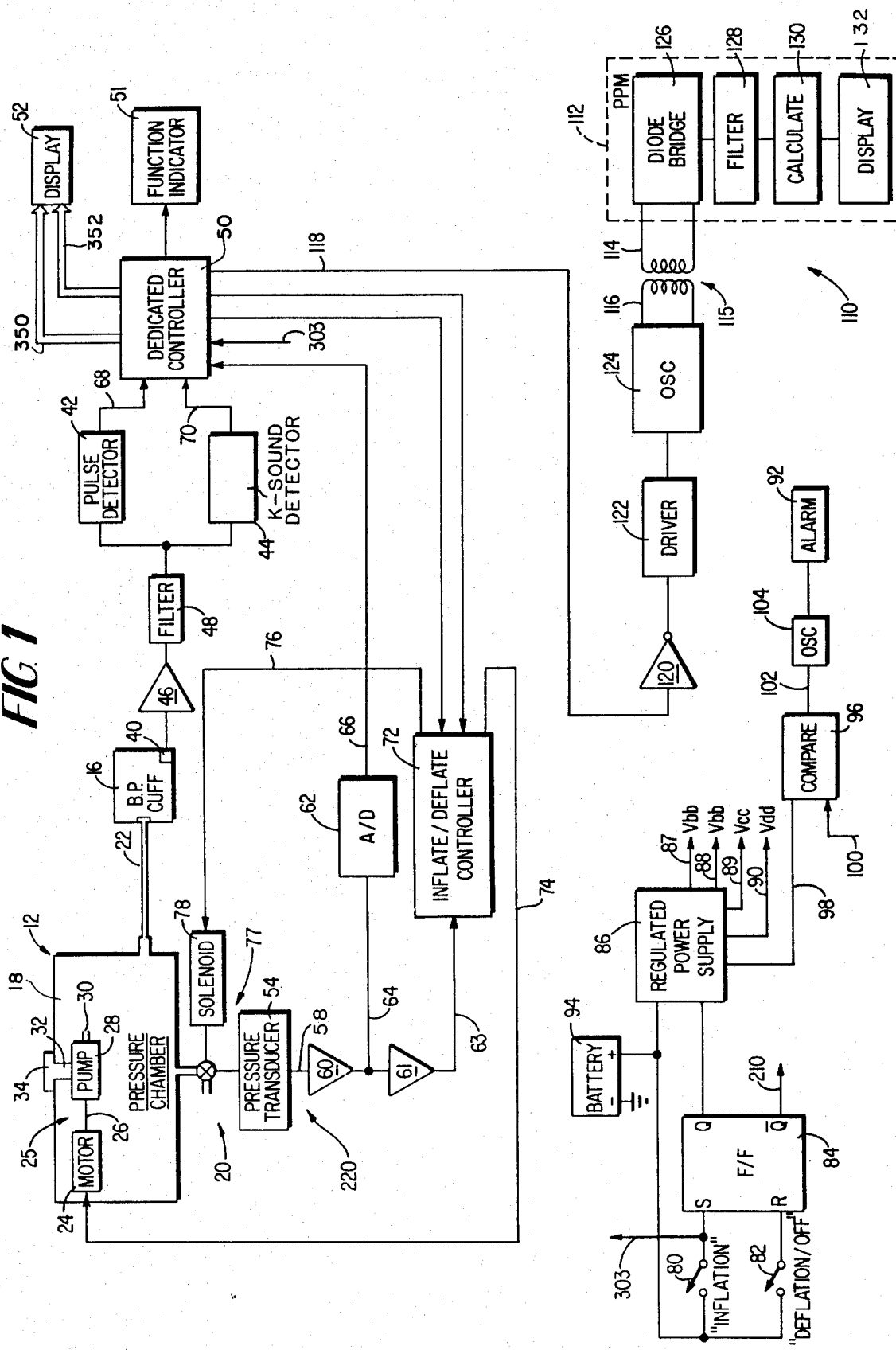
FIG. 1 is a schematic diagram of an embodiment of the blood pressure system.

In describing a preferred embodiment of the invention illustrated in the drawings, specific terminology will be resorted to for the sake of clarity. However, the invention is not intended to be limited to the specific terms so selected, and it is to be understood that eah specific term includes all technical equivalents which operate in similar manner to accomplish a similar purpose.

FIG. 1 illustrates, in schematic form, the basic elements constituting the inventive blood pressure system, which is generally designated as 10. The blood pressure system 10 basically comprises a pressure cuff system 12 for accomplishing occlusion and the subsequent opening of an artery in a patient being monitored, and an electronic system 14 for controlling the pressure cuff system and for displaying the systolic and diastolic measurements.

With regard to the cuff pressure system 12, an inflatable pressure cuff 16 is provided and is positioned by wrapping the cuff in a deflated state about the patient's upper arm. Cuff 16 is suitably positioned to restrict the brachial artery when the cuff is inflated. A pressure chamber 18 provides compressed air by way of a flexible hose 22 to inflate the cuff 16. Contained within the pressure chamber 18, a motor 24 turns a drive shaft 26 to activate a pump 28 which produces compressed air at a pump output 30. In order to produce the compressed air at pump output 30, the pump used the outside atmosphere as a source of air. The outside air is received in the pump through a conduit 32 after passing through an air filter 34.

With regard to the electronic system 14, a microphone 40 is disposed within the cuff 16 so that when the cuff is placed about the arm, the microphone rests against the skin in close proximity to the brachial artery. The microphone is used to sense Korotkoff sounds in much the same way that a stethoscope does. The output of the microphone is fed to a pulse detector 42 and a K-sound (Korotkoff sound) detector 44 after passing through an amplifier 46 and a filter 48.

A microcomputer 50 acts as a dedicated controller for controlling the operation of the blood pressure system 10 and as a means for processing various digital signals to produce a reading of systolic and diasatolic pressure on a display 52. The microcomputer 50 performs other functions which will be described in greater detail hereinafter.

A pressure transducer 54 is operatively associated with the pressure chamber 18 by way of a bleed valve 20 in order to monitor the changing pressure within the chamber. The pressure transducer 54 converts the pressure within the chamber to an electrical signal appearing on line 58. The signal on line 58 passes thorugh amplifier 60 and then into an analog-to-digital converter 62. The signal appearing at the input 64 of the analog-to-digital converter is an analog voltage which is representative of the pressure in millimeters of mercury both in the pressure chamber and in the blood pressure cuff.

The output of the analog-to-digital converter 62 is fed into the microcomputer 50 on lines 66. In like manner, the output of the pulse detector 42 is fed into the microcomputer on lines 68, while the output of the K-sound detector 44 is fed into the microcomputer on lines 70. The digital data appearing on lines 66, 68 and 70 provide the microcomputer 50 with the necessary information to automatically calculate and display a proper blood pressure reading.

An inflate/deflate controller 72 monitors the output from the pressure transducer 54 after being amplified by amplifiers 60 and 61, and, in response to signals received from the microcomputer, causes an inflation or deflation of the blood pressure cuff 16. Inflation is accomplished when the controller 72 produces a signal on lines 74 which activates the motor 24 in order to increase the pressure within the chamber and thereby increase the pressure within the cuff 16. The deflate cycle is accomplished when the controller 72 produces a signal on lines 76 which activates a solenoid 78 associated with the bleed valve 20 in order to vent the pressurized air contained both in the pressure chamber 18 and the blood pressure cuff 16.

The blood pressure system 10 contains two manual switches. The first switch 80, which is labelled "INFLATION", initiates a complete blood pressure measuring cycle within the blood pressure system 10. Basically, a complete blood pressure measuring cycle consists of inflating the cuff 16 with a pressure somewhat higher than the pressure necessary to occlude the brachial artery, and then slowly deflating the cuff while monitoring the K-sounds characteristic of systolic and diastolic pressure.

The second switch 82, which is labelled "DEFLATE/OFF", releases air pressure from the chamber 18 and the cuff 16, and simultaneously turns the instrument off. The switches 80 and 82 are connected respectively to the set and re-set inputs of a flip-flop 84, which produces at its Q output a signal for activating a regualted power supply 86. The regulated power supply which is powered by a battery 94, contains four output supply lines. A voltage Vbb, which is typically five volts, appears at the output of the first two supply lines 87 and 88. A voltage Vcc, which is typically 8.6 volts, appears at line 89, and a voltage Vdd, which is typicaly 3.6 volts, appears on line 90. As will be explained in greater detail hereinafter, these voltages are used to power the various components of the blood pressure system.

An alarm 92 is provided to warn the user should the battery 94, used to power the system, become low. A comparator 96 monitors the battery voltage as received on line 98 and compared it with a reference signal appearing on line 100 to determined if the battery voltage is falling below a predetermined value. If so the comparator issues a signal on lines 102 to activate an oscillator 104 which in turn causes the alarm 92 to issue a signal.

As part of the blood pressure instrument, there is also provided a pulse transfer system, generally designated as 110, for receiving and processing information from the microcomputer 50 in order to produce a display of heart rate in beats-per-minute. Basically, the pulse transfer system 110, in addition to the blood pressure system 10, employs a separate physiological parameter measuring system (PPM) 112, which normally measures temperature, pressure and respiration. One such PPM system is that dislosed in co-pending U.S. patent application Ser. No. 935,642, filed Aug. 21, 1978, now U.S. Pat. No. 4,232,682 incorporated by reference herein.

The PPM 112 employs an inductive battery charging device. In order to charge the batteries in the PPM, inductive coupling takes place between a coil in the PPM and a mating coil in a battery charging device (not shown). The same coil 114 used in the battery charging mode of the PPM is employed with the blood pressure instrument 10 in order to receive information from the microcomputer 50. A second inductive coil 116 is provided in the electronic system 14. The microcomputer 50 receives the signal from the pulse detector 42 on line 68. The microcomputer then processes this signal to produce a signal on lines 118 which represents heart rate in beats-per-minute. The signal on line 118 is buffered by inverter 120 and then fed to a driver 122, which triggers an oscillator 124 at a rate equal to the signal produced on line 118. The output of the oscillator 124 is fed to induction coil 116. An inductive coupling takes place between coils 114 and 116. The signal received by coil 114 is passed through a diode bridge 126 then to a filter/comparator 128, and finally to a microcomputer 130 contained within the PPM in order to produce a display of the pulse rate in beats-per-minute on the display 132 of the PPM. When the pulse rate information is being transferred by the blood pressure instrument, the pulse rate junction in the PPM is shut off automatically to avoid double readings.

Figure 6:
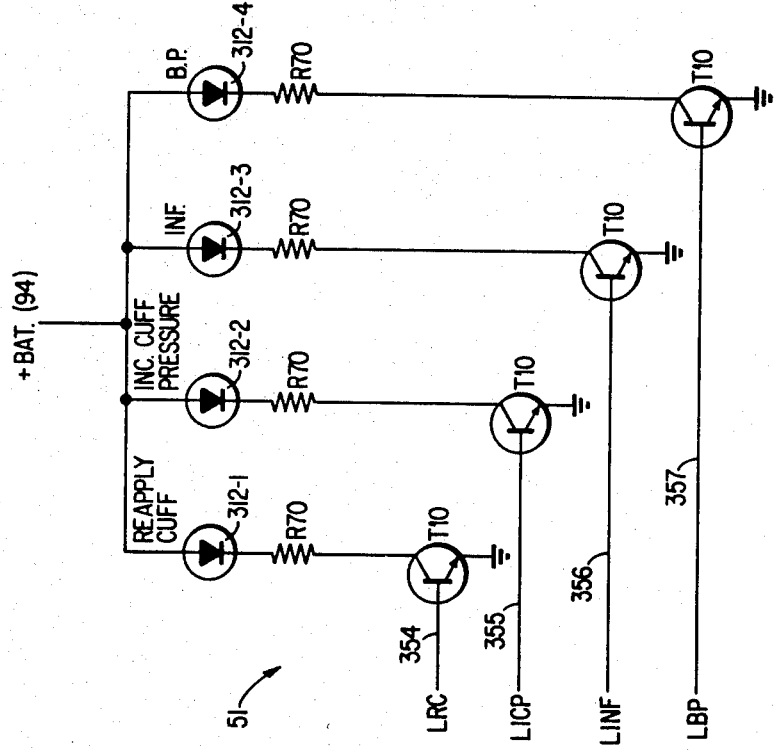
FIG. 6 is a schematic diagram showing an embodiment of a function indicator for use in the embodiment of the blood pressure system shown in FIG. 1.

With reference to FIG. 36, a suitable housing for the blood pressure system 10 is shown. The housing, generally designated as 1000, basically comprises a pedestal 1002, which supports a main body portion 1004. Mounted to the bottom of the pedestal are a series of wheel canisters 1006, which provide a means for easy movement of the blood pressure system. Atop the main body portion 1004 is a display portion 1008 which contains a display panel 1010. The systolic and diastolic blood presure readings are displayed on the panel 1010. In addition, the functions indicated in FIG. 6 are also displayed.

Preferably, the pump chamber 18 and its associated mechanical parts are located within the main body portion 1004, with the electronic system 14 being located in the display portion 1008.

Attached to the main body portion 1004 is the flexible tubing 22 which is attached, at its other end, to the blood pressure cuff 16.

A space is provided on the top of the main body portion 1004 to receive the physiological parameter measuring system (PPM) 112 shown in phantom. The PPM contains a display panel 1014 for displaying the pulse in beats per minute as will be described hereinafter.

As can be seen, the blood pressure system may be used with or without the PPM 112. In addition, the blood pressure system is a completely portable battery-powered unit which may be easily moved from patient to patient, during the taking of blood pressure measurements. In addition, the blood pressure system provides a convenient means for transporting the PPM 112 so that, while blood pressure readings are being taken, the additional physiological parameters of temperature, pulse, and respiration may also be taken.

With reference to the drawings, the details of the various elements constituting the blood pressure instrument 10 will now be described.

Sound Sensor, Pulse Detector, and K-Sound Detector

Figure 2:
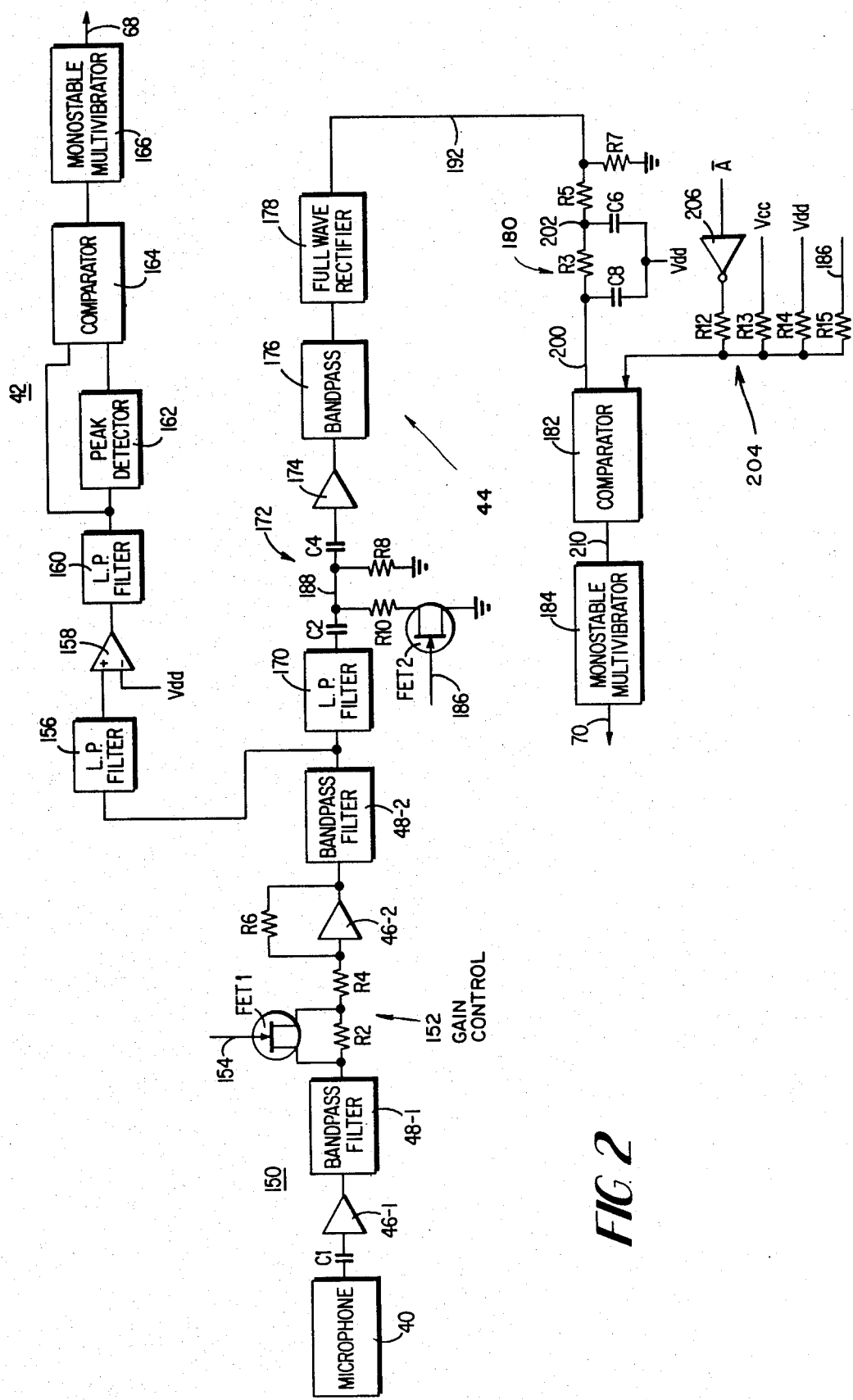
FIG. 2 is a schematic diagram illustrating embodiments of a sound sensor, a pulse detector, and a K-sound detector for use in the embodiment shown in FIG. 1.

With reference to FIG. 2, the sound sensor 150 basically comprises a microphone 40, a pair of amplifiers 46-1 and 46-2, and a pair of band-pass filters 48-1 and 48-2. A gain control 152 is also provided.

The microphone 40 is preferably a commercially available contact microphone having a frequency response in the frequency range of 0.5 Hz to 150 Hz. In use, the microphone is typically placed between the cuff 16 and the arm of the individual so that the microphone is disposed in close proximity to the brachial artery. The output signal of the microphone is coupled through capacitor C1 to amplifier 46-1 where the signal is increased by a factor of approximately 9, and then fed into the band-pass filter 48-1. The frequency range of band-pass of the filter 48-1 is typically between 0.5-150 Hz. The output of the band-pass filter 48-1 is then fed to amplifier 46-2 for a further increase in signal strength of approximately 1.5 times, in a normal mode, or 3.3 times, in a high gain mode. The output of amplifier 46-2 is simultaneously fed to pulse detector 42 and K-sound detector 44 via band pass filter 48-2.

In sensing circuit 150, gain selection in amplifier 46-2 is made by gain control circuit 152. In the gain control circuit, resistors R2 and R4 are connected in series between the output of band-pass filter 48-1 and the input of amplifier 46-2. Resistor R2 is also connected in parallel with the drain and source of a field effect device FET 1. To complete the circuit, a resistor R6 is connected between the input and output of amplifier 46-2. Gain selection is accomplished by turning on field effect transistor FET 1. In the normal mode, the transistor FET 1 is normally off and the gain of amplifier 46-2 is controlled by resistors R2, R4 and R6. This is fine for the detection of normal K-sounds. However, should the K-sounds detected by the microphone be of an abnormally low intensity, then the microcomputer 50 produces an HI-GAIN signal on line 154 to cause the field effect device FET 1 to conduct and, in effect, short out the resistor R2. The gain of amplifier 46-2 in then controlled only by resistors R4 and R6, and a gain of approximately 3.3 is produced.

The output of the band-pass filter 48-2 is then simultaneously fed to both the puse detector 42 and the K-sound detector 44. The pulse detector 42 takes the raw data from the sound sensor 150 and produces a digital signal on lines 68 that corresponds to the pulse, which is the rhythmic throbbing caused by the regular contraction and dilation of the wall of the brachial artery due to the systolic wave emanating from the heart. Likewise, the K-sound detector 44 takes the raw data from the sound sensor 150 and processes it to produce a digital signal on lines 70 that corresponds to K-sounds.

The output signal fo the amplifier 46-2 enters the pulse detector via filter 48-2, and first passes though a low-pass filter 156, which is tuned to attenuate frequencies above approximately 10 Hz. The output of the low-pass filter is then fed to the non-inverting input of differential amplifier 158. The inverting input of amplifier 158 receives the voltage Vdd. The output of amplifier 158 is a difference signal multiplied by approximately 10. Any high frequencies present are then attenuated by a low-pass filter 160, which is tuned to have a low-pass characteristic within the range of approximately 0.5–10 Hz. The output of the low-pass filter 160 is simultaneously fed to a comparator 164 and a peak detector 162. Comparator 164 is triggered positive when the signal output of low-pass filter 160 increases above the average D.C. level of the peak detector. The comparator output goes negative when the output of filter 160 decreases to a value ½ of the signal peak. The output of the comparator triggers a mono-stable multivibrator 166 to produce at its output 68, a digital signal in the form of a square wave pulse which corresponds to each heart beat. As stated before, the digital signal on line 68 is fed into the microcomputer 50 for processing.

The output of amplifier 46-2, via filter 48-2, is also fed into the K-sound detector 44 and first passes through a low-pass filter 170, which is turned to attenuate frequencies above approximaely 100 Hz. The output of the low-pass filter 170 is then received by a special high-pass filter 172, which is adapted to respond to a signal from the microcomputer 50 appearing on line 186 to selectively change the pass-band of the filter depending on whether the K-sound detector 4 is operating to detect systolic or diastolic K-sounds. The high-pass filter 172 comprises a pair of capacitors C2 and C4 in series. A resistor R8 is connected between ground and the common junction 188 of the two capacitors. A resistor R10 in series with a field effect device FET 2 is connected between ground and the common junction 188. The field effect device FET 2 is normally off so that the filter 172 has a pass-band of between 40–100 Hz for diastolic detection. In response to a signal received on line 186 from the microcomputer 50, the field effect device FET 2 is caused to conduct, thus introducing the resistor R10 into the filter circuit. The filter 172 then exhibits a band-pass characteristic of between 20–100 Hz for systolic detection. The selection by the microcomputer of the mode of operation for the high-pass filter 172 will be described in greater detail hereinafter when discussing the microcomputer 50.

The output of the band-pass filter 172 is received by a band-pass filter 176 via amplifier 174. Filter 176 has a band-pass characteristic of between 20–100 Hz. Because K-sounds are sometimes positive and negative going, the output of the amplifier 174 is fed to a full wave rectifier 178 in order to convert the negative going K-sound signals into positive signals. In this way, the signal appearing at the output of the full wave rectifier 178 on lines 192 is positive for all K-sounds.

The signal on line 192 represents each K-sound as a series of closely spaced spikes. An envelope circuit 180 in effect traces around the spikes to produce a signal which is as wide as the spikes. This signal appears on lines 200. The envelope circuit 180, which is basically a filter, comprises a pair of resistors R3 and R5 in series. A resistor R7 is connected betwen ground and the input of the envelope circuit. A capacitor C6 is connected between the voltage source Vdd and the common connection 202 between the resistors R3 and R5. A third capacitor C8 is connected between the voltage source Vdd and the output of the envelope circuit.

The output of the envelope circuit is received at one input of a comparator 182. The other input of the comparator receives a threshold voltage which varies according to the mode of operation of the blood presure instrument. The threshold voltage is determined by a resistor network 204 which consists of four resistors R12 through R15, one end of each being connected to the input of the comparator. The other end of resistor R12 receives a signal from the microcomputer 50 via inverter 206. The free ends of resistors R13 and R14 are connected respectively to voltage sources Vcc and Vdd. The free end of resistor R15 receives a signal from the microcomputer 50 on line 186. This is the same signal that is fed to the high-pass filter 172.

As will be explained in greater detail hereinafter, the level of the threshold voltage is adjusted according to the selective mode of operation of the blood pressure insturment. During the initial inflation cycle of the blood pressure instrument, the threshold voltage is at its highest level. During the deflation cycle when systolic K-sounds are being detected, the threshold voltage is at a lower predetermined level. During the deflation cycle when diastolic K-sounds are being detected, the threshold voltage is at its lowest level. The comparator 182 compares the output of the envelope circuit 180 with the threshold voltage in order to produce a signal on lines 210, which triggers a monostable multi-vibrator to produce on lines 70 a digital signal indicative of the detection of a K-sound. The signal on line 70 is fed into the microcomputer 50 for subsequent processing.

Pressure Sensor and Signal Converter

With reference to FIG. 3, the pressure sensor 220 basically comprises a pressure transducer 54, which is typically a strain gauge of the piezoelectric type, coupled to a pair of amplifiers 60-1 and 60-2, configured as voltage followers, which are in turn connected to an amplifier 60-3 configured as an integrator.

The pressure transducer 54 is of conventional design and may take the form of any of the well known devices such as a piezoelectric transducer. The pressure transducer 54 responds to the pressure within the chamber 18 to produce an electrical voltage across its plus and minus outputs. The pressure transducer 54 is schematically represented by four resistors R71 through R74 configured in a bridge network. The common connection of resistors R71 and R72 provides the minus output, and the common connection between resistors R72 and R74 provides the plus output. The common connection between resistors R72 and R73 is at ground. The common connection between resistors R71 and R74 is connected by way of resistor R9 to voltage Vcc which in turn is connected to ground by way of capacitor C10. The common connection between resistors R71 and R74 is also connected to the emitter of transistor T1 via resistor R16. The collector of transistor T1 is connected to the positive side of the battery 94, while the base of transistor T1 is connected to the $\overline{Q}$ output of flip-flop 84 (see FIG. 1) via resistor R17 and line 210.

When the blood pressure system 10 is idle, the $\overline{Q}$ output of flip-flop 84 is normally high. This, in turn, causes the transistor T1 to conduct, thereby supplying power to the pressure transducer 54, so that the pressure transducer is always in a ready state. Upon initiation of the inflation cycle, the $\overline{Q}$ output of flip-flop 84 goes low, thereby turning off transistor T1 and thus removing the battery power form the pressure transducer 54. At the same time, the Q output of flip-flop 84 goes high, activating power supply 86 and thereby supplying voltage Vcc to pressure transducer 54 by way of resistor R9.

The plus output of the pressure transudcer 54 is connected to the input of amplifier 60-1 which is configured as a voltage follower. In like manner, the negative output of the pressure transducer is connected to the amplifier 60-2, which is also configured as a voltage follower. The outputs of amplifier 60-1 and 60-2 are fed respectively into the plus and minus inputs of differential amplifier 60-3 which includes a capacitor C12 and resistor R18 in parallel. The output of amplifier 60-3 appears on line 64 as an analog voltage which is representative of the pressure in millimeters of mercury both in the pressure chamber and in the blood pressure cuff. The analog signal is then fed to analog-to-digital converter 162. The digital output of the analog-to-digital converter 62 is fed to the microcomputer 50 on lines 66.

The output of amplifier 60-3 is also fed via resistor R19 to the positive input of amplifier 61, which through the arrangement of resistors R20 and R21 is configured as a non-inverting amplifier having a gain of approximately 10. The output of amplifier 61 appears on line 63 and is fed to the inflate/deflate controller 72.

Inflate/Deflate Controller

Figure 4:
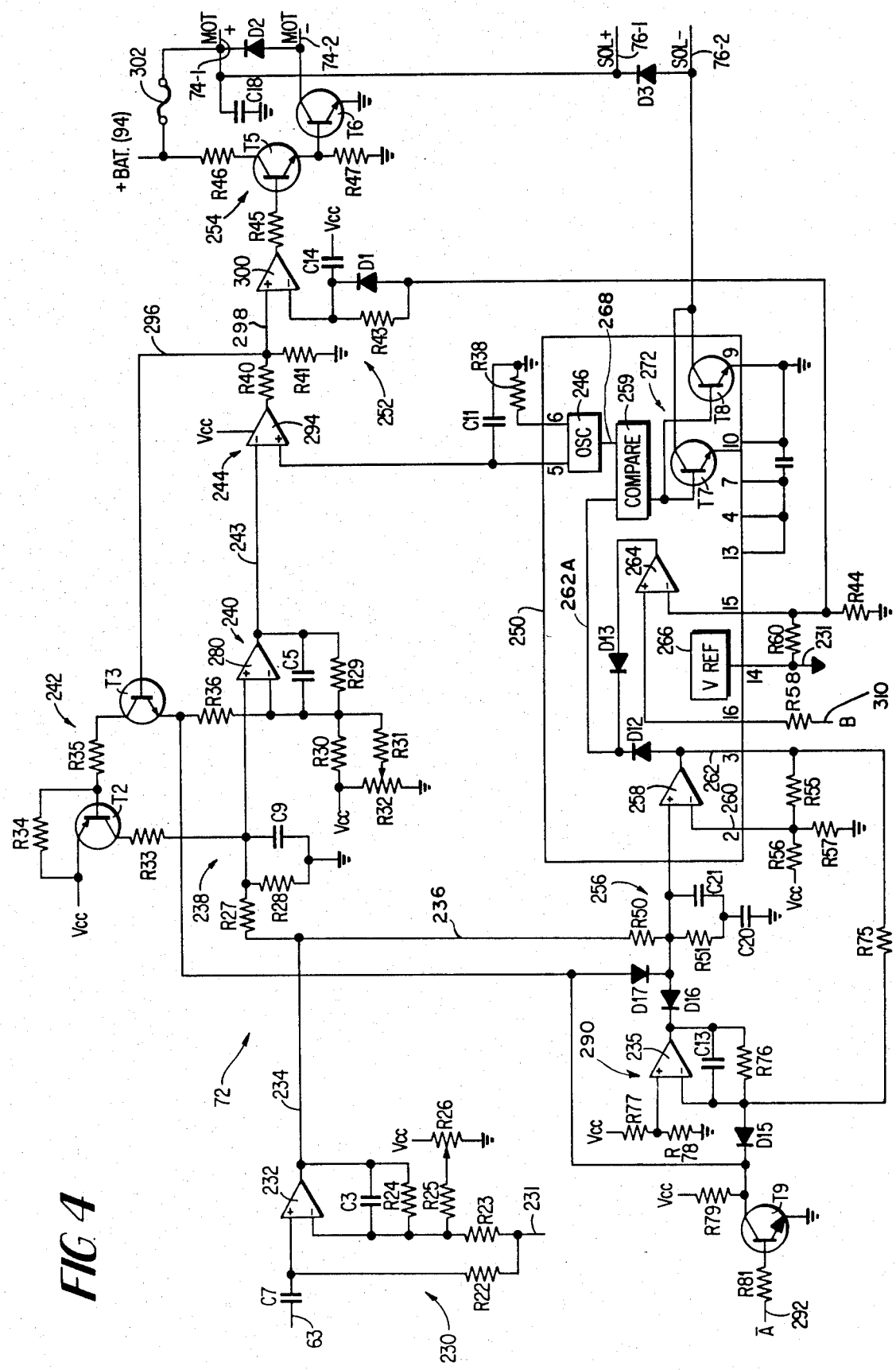
FIG. 4 is a schematic diagram showing an embodiment of the inflate/deflate controller shown in FIG. 1.

FIG. 4 is a detailed schematic diagram of the inflate/deflate controller 72. With reference to this figure and FIG. 1, it can be seen that the analog voltage signal derived from the pressure transducer 54 is received on line 63 and processed by the controller 72 to produce at the output of the controller, on lines 74-1 and 74-2, a signal to control the motor 24. The controller 72 has another output produced on lines 76-1 and 76-2 to control the solenoid 78 which in turn controls the bleed valve or solenoid valve 20.

Returning now to FIG. 4, the signal appearing on line 63, derived from the pressure transducer, is an analog signal of changing voltage in proportion to the pressure within the cuff 16 and the pressure chamber 18. The signal on line 63 passes through a differentiator and comparator 230, the output of which appears on line 234.

The signal on line 234 then branches out on line 236 and is fed through a low-pass filter 238. The output of the low-pass filter 238 is fed to the non-inverting input of comparator 240. The inverting input of comparator 240 receives a signal from a pump initialization circuit 242. The output of the comparator 240 appears on line 243. The signal on line 243 is fed into the inverting input of comparator 244. The non-inverting input of comparator 244 receives a ramp voltage generated by the oscillator 246 which forms a part of the pulse width modulation control circuit 250. The control circuit 250 will be discussed in greater detail hereinafter. However, at this point, it should be pointed out that the control circuit 250 is an integrated circuit manufactured by Texas Instruments and bears the designation TL494C.

The output of comparator 244 is fed into a time delay circuit 252. The output of the time delay circuit is then fed to a driver 254 which contains output leads 74-1 and 74-2 for connection to motor 24.

Returning now to line 234, the signal on that line passes through a low-pass filter 256 and into the non-inverting input of an amplifier 258 contained within the control circuit 250. The inverting input of amplifier 258 receives a reference signal on line 260 which is varied by an error feedback signal appearing on line 262.

A second amplifier 264 has its output connected to line 262A through diode D13. Inverting input of amplifier 264 receives a reference signal derived from a voltage source 266. The non-inverting input of amplifier 264 receives a signal from the microcomputer 50.

The outputs of the two amplifiers 258 and 264 are combined on line 262A via diodes D12 and D13. The oscillator 246 produces a ramp signal on line 268 which is the output of an inverter 270. The signals on lines 262A and 268 are fed within the control circuit 250 to a pair of power transistors 272 which act as drivers for the solenoid 78. The control signals for the solenoid appear on lines 76-1 and 76-2.

The details of the various circuits constituting the inflate/deflate controller 72 will now be described with reference again to FIG. 4. The signal on line 63 is fed to the non-inverting input of amplifier 232 via capacitor C7. A resistor R22 connects the non-inverting input of amplifier 232 with the reference voltage 266 of control circuit 250 via line 231. A parallel arrangement of resistor R24 and capacitor C3 is connected between the inverting input of amplifier 232 and the output of the amplifier. A resistor R23 connects the reference voltage 266 to the inverting input of amplifier 232. Finally, resistor R25 connects the inverting input of amplifier 232 with a variable resistance R26 which in turn is connected between the voltage source Vcc and ground.

The low-pass filter 238 comprises a resistor R27, one end of which receives the signal on line 236 and the other end of which is connected to a parallel arrangement of a resistor R28 and a capacitor C9 both of which have one end connected to ground.

The heart of comparator 240 is an amplifier 280, the non-inverting input of which receives the output of the filter 238. A parallel arrangement of resistor R29 and capacitor C5 is connected between the inverting input of amplifier 280 and the output of the amplifier. The inverting input of amplifier 280 is also connected to a source of voltage Vcc via resistor R30. Resistor R31 connects the inverting input of amplifier 280 with a variable resistor R32 which is connected between voltage source Vcc and ground.

The pump initialization circuit 242 basically comprises a pair of transistors T2 and T3. Transistor T2 has its emitter connected to voltage source Vcc, its collector connected to the non-inverting input of amplifier 280 via resistor R33, and its base connected to voltage source Vcc via resistor R34. Transistor T3 has its collector connected to the base of transistor T2 via resistor R35, its emitter connected to the inverting input of amplifier 280 via resistor R36, and its base connected to the output of comparator 244. The emitter of transistor T3 is also connected to the function selection circuit 290.

At the heart of the function control circuit 290 is amplifier 235. A resistor R77 is connected between the non-inverting input of amplifier 235 and the voltage Vcc. Also, a resistor R78 is connected between the non-inverting input of the amplifier and ground.

A parallel arrangement of resistor R76 and capacitor C13 is connected between the output and the inverting input of amplifier 235. Line 262 of control circuit 250 is also connected to the inverting input of amplifier 235 via resistor R75.

A transistor T9 has its base connected to the microcomputer 50 via resistor R81. The emitter of transistor T9 is connected to ground, and the collector of transistor T9 is connected to the inverting input of amplifier 235 via diode D15. A resistor R79 is connected between the collector of transistor T9 and the voltage Vcc. The collector of transistor T9 is also connected to the emitter of transistor T3 of circuit 242, and to a diode D17 which has its cathode connected to the input of filter 256. Another diode D16 has its cathode connected to the output of amplifier 235 and its anode connected to input of filter 256.

The comparator 244 is an inverting open loop amplifier 294 which receives at its inverting input the control signal on line 243. The non-inverting input of amplifier 294 receives a saw tooth voltage generated by the oscillator 246 of control circuit 250. The frequency of oscillator 246 is set by capacitor C11 and resistor R38. Capacitor C11 has one end connected to the non-inverting input of amplifier 294 and the other end connected to ground, while the resistor R38 has one end connected to the oscillator at pin 6 of control circuit 250 and the other end connected to ground.

The output of amplifier 294 passes through a voltage divider formed by resistors R40 and R41 and then simultaneously to the base of transistor T3 on line 296 and to the delay circuit 252 on line 298.

The delay circuit 252 comprises an amplifier 300 which receives at its non-inverting input the signal on line 298. A time constant determined by capacitor C14 and resistor R43 is introduced into the amplifier 300 at the non-inverting input of the amplifier in order to produce a 0.5 second delay in the amplifier 300. The capacitor C14 is connected between a voltage source Vcc and the inverting input of amplifier 300. Resistor R43, in series with resistor R44, is connected between the inverting input of amplifier 300 and ground. A diode D1 is connected in parallel with resistor R43.

The output of amplifier 300 is fed to pump driver circuit 254 via resistor R45. The pump driver 254 basically comprises two transistors T5 and T6. Transistor T5 has its base connected to resistor R45, its collector connected to the battery 94 via resistor R46, and its emitter connected to the base of transistor T6 and to ground via resistor R47. Transistor T6, in turn, has its collector connected to line 74-2 and its emitter connected directly to ground.

Line 74-1 is connected to line 74-2 by a diode D2. Line 74-1 is also connected to ground via capacitor C18 and to the battery by way of a suitable fuse 302.

The low-pass filter 256 includes a capacitor C20 and a pair of resistors R50 and R51, all of which are connected in series between ground and the output of the differentiator and the comparator 230. The filter 256 also includes a capacitor C21 connected in parallel with resistor R51.

With reference to the control circuit 250, feedback line 262 is connected to the inverting input of amplifier 258 via resistor R55. The inverting input of amplifier 258 is also connected to a voltage source Vcc by way of resistor R56 and to ground by way of resistor R57.

The second amplifier 264 has its non-inverting input connected to the microcomputer 50 by way of resistor R58. The output of the reference voltage 266 which appears on pin 14 of control circuit 250 is connected to the inverting input of amplifier 264 by way of resistor R60.

The drive signal for the solenoid 78 appears on lines 76-1 and 76-2. These lines are connected together by diode D3. Additionally line 76-1 is connected to the battery 94 by way of fuse 302.

The operation of the inflate/deflate controller 72 will now be described in detail.

The analog voltage signal, derived from the pressure transducer 54, is received on line 63 by a differentiator consisting of capacitor C7 and resistor R22. The voltage presented to the non-inverting input of comparator/amplifier 232 is the sum of a stable reference voltage 266 received on line 231 from the control circuit 250 and a presettable offset voltage derived from variable resistor (trimmer) R26. The output of the differentiator which appears as a voltage across resistor R22 is proportional to the rate of change of transducer output (i.e., rate of change of pressure). A resistor network R23 and R25 in association with variable resistor (trimmer) R26 sets the gain and offset voltage derived from amplifier 232. Capacitor C3, in association with resistor R24, forms a low-pass filter pole which reduces the short term signal fluctuations on line 234 and ensures closed loop stability. The signal at 234 is a voltage which varies in proportion to the difference between the actual rate of change of pressure and the desired rate of change of pressure.

The signal on line 234 branches to line 236 towards circuits 238 and 240 which control inflation via the pump and motor assembly 25 (FIG. 1). The same signal branches to filter network 256 and control circuit 250 to control deflation and "dump" of the pneumatic system via the solenoid valve 20. Both these circuits employ proportional control using a constant frequency variable duty cycle arrangement. A constant frequency oscillator 246 is controlled by frequency determining components capacitor C11 and resistor R38. The resulting positive going sawtooth output (2.5 kHz) is used to control the solenoid 78 and, in turn, the valve 20 and, via the non-inverting input of 294, the pump motor 24.

During the deflation cycle, the solenoid valve assembly 77 is under closed loop servo control. Circuits shown in FIG. 4 within this loop are serially 232, 256 and 250. The "error" signal on line 234 is presented to the non-inverting input of amplifier 258 via a low-pass filter consisting of resistors R50 and R51 and capacitor C20. Capacitor C21 is provided to reduce high frequency noise.

Gain and offset of amplifier 258 are set by resistors R55, R56 and R57. Outputs of amplifiers 258 and 264 are combined via diodes D12 and D13 so that, providing the non-inverting input of 264 is held low, the voltage on line 262A remains a diode drop below amplifier output 262. The voltage on line 262A is presented to a comparator 259 together with the sawtooth waveform derived from oscillator 246. The output of the comparator is in the form of a pulse train at a repetition rate determined by oscillator 246 and a duty cycle determined by amplifier output 262 as required to maintain a constant deflation rate of 3 mmHg/sec. (Closed loop servo operation). Two parallel wired power transistors T7 and T8 transfer this duty cycle controlled switching voltage to the solenoid 78 via line 76-2.

The variable duty cycle waveform presented to the solenoid 78 on line 76-2 at the collectors of power transistors T7 and T8 will be at the repetition rate defined by oscillator 246. As pressure decreases during the deflation cycle, the ratio of off time (76-2 high) to on time (76-2 low) increases. It is typically 50%. Fast deflate or "dump" mode is enabled by "B" signal from the microcomputer 50 via line 310. When a logical "1" appears on 310, the output of open loop amplifier 264 goes high and, regardless of the signal on 262, line 262A is taken to the high state, fully opening the solenoid valve 20. This condition will override the servo controlled deflation rate at all times.

During the inflation cycle, the pump motor 24 is under closed loop servo control. Circuits shown in FIG. 4 within this loop are serially 232, 238, 240, 244, 252, and 254. Circuits 242 and 290 will be discussed separately. The "error" signal on line 234 is presented to the non-inverting input of amplifier 280 via a low-pass filter 238 consisting of resistors R27 and R28, and capacitor C9. Gain and offset of amplifier 280 is determined by resistors R30, R31, R32 and R29. Capacitor C10 C5 is provided to reduce high frequency noise and to ensure closed loop stability. Inflation rate is preset by variable resistor R32. The output of amplifier 280 appears on line 243, which is connected to the inverting input of comparator 294. The non-inverting input of this comparator is fed from the sawtooth oscillator 246 so that a square waveform with duty cycle controlled by the signal on line 243 is obtained at the comparator output on line 298. The dc voltage level on line 262 determines the duty cycle which is at a repetition rate determined directly by oscillator 246.

During the inflation cycle, open loop amplifier 300 merely inverts the variable duty cycle waveform for presentation to the pump motor 24 via driver T5 and power transistor T6. Network 252 merely delays application of motor power immediately following system power up. (Hold off time is determined by resistor R43 and capacitor C14; fast reset is answered by diode D1.) By this means, the pulse voltage presented to the pump motor 24 on line 74-2 is varied automatically so that its mean d.c. level regulates motor speed to ensure a constant rate of inflation. The nature of the waveform on line 74-2 is similar to that presented to the solenoid valve on line 76-2.

Pump initialization circuit 242 provides a means to accelerate "locking" of the inflation servo so that delays in starting the pump motor 24, otherwise caused by the dominating circuit time constant, are minimized. Without this circuit, a long delay (several seconds) would be evident between a "pump-start" command and actual start-up of the pump. Instead of waiting for capacitor C9 to slew into the operating range of amplifier 280 at the commencement of the inflation cycle, circuit 242 maintains a charge of capacitor C9, which sustains the inflation loop just below motor switch-on at all times when the pump motor 24 is switched off. In the deflation or "dump" modes, transistor T9 has its collector low and transistor T3 has its emitter near ground. Transistors T3 and T2, amplifier 240 and comparator 244 form, in this mode, a closed loop such that a series of narrow pulses (at the oscillator repetition rate) are generated on line 296. This pulse train is presented to capacitor C9 via switching transistors T3 and T2. The resulting "smoothed" charge on C9 results in a mean voltage on the non-inverting input of amplifier 280 sufficient to maintain line 298 below the threshold of comparator 300, but within the linear range of amplifier 280. When the inflation mode is selected, the collector of transistor T9 goes high, reverse biassing transistor T3, so that transistors T2 and T3 become inoperative and capacitor C9 quickly slews into the linear control range of the pump motor. An additional motor start offset is ensured by resistor R36.

A similar mechanism is established for the deflation control circuits by means of circuit 235. During the inflation mode, the microcomputer control signal on line 292 forces the collector of transistor T9 to the high state. In this mode, circuits 235, 256 and 258 form a closed loop which maintains the output of amplifier 258 on line 262 at a low d.c. voltage within the linear range of amplifier 258, but sufficient to hold the solenoid valve closed until the deflate mode is selected. By this means, a charge is sustained on capacitor C20 which eliminates the need for excessive slewing, with a corresponding delay, whenever the deflate mode is entered. Diodes D15, D16 and D17 provide isolation from circuit 250 during the deflating cycle when control of the solenoid valve control voltage is restored to line 234.

Microcomputer, Display, and Function Indicator

Figure 7:
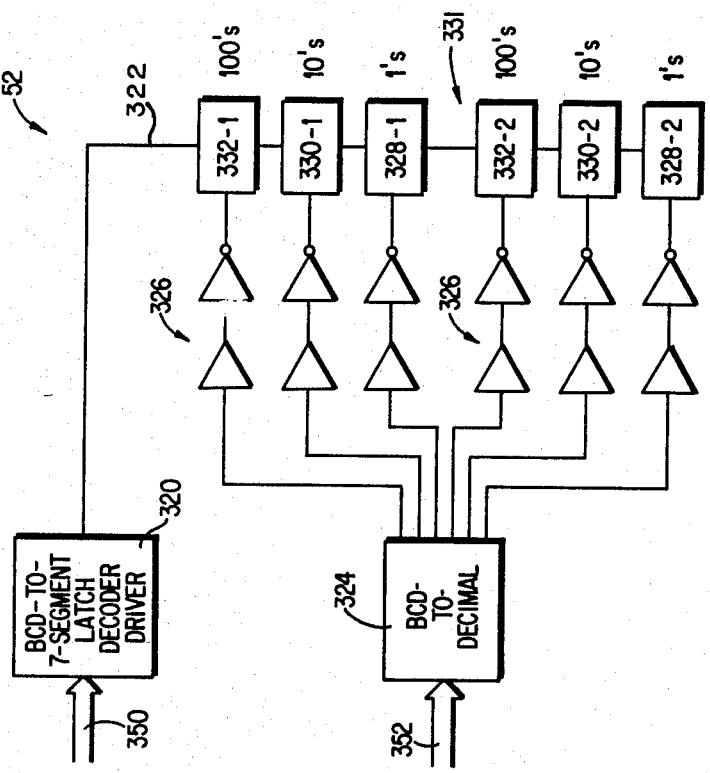
FIG. 7 is a schematic diagram of a display for use with the embodiment of the blood pressure shown in FIG. 1.

With reference to FIGS. 5 through 7, the portion of the blood pressure instrument 10 which processes the raw data to produce a visual readout of systolic and diastolic pressure is shown. The heart of this portion of the system is the microcomputer 50, which typically comprises a 2,000 word, 8 bit dedicated controller. One such microcomputer which has the characteristics desirable for application in the blood pressure instrument carries the designation No. 3870 and is manufactured by such companies as Mostek, Fairchild, and Motorola.

With reference to FIGS. 1 and 5 through 7, when switch 80 is closed, to indicate the selection of the inflation mode, a signal appearing on line 303 activates the microcomputer 50. The microcomputer 50 receives, on lines 66, the raw digital data from the analog-to-digital converter 62, which produces a digital representation of the pressure within the chamber 18 as sensed by the pressure transducer 54. Lines 68 contain the raw digital data produced by the pulse detector 42. The data on lines 66 is indicative of the heart rate in real time as sensed by the microphone 40. Finally, the microcomputer 50 receives, on lines 70, the raw digital data from the K-sound detector 44. This data represents, in digital form, the real time K-sounds sensed by the microphone 40.

The microcomputer 50 processes the data from the pulse detector 42, appearing on lines 68, to produce an output signal on line 118 which is used in the heart rate monitoring system, which will be described in greater detail hereinafter.

The microcomputer 50 is pre-programmed to receive the data on lines 70 from the K-sound detector and on lines 66 from the analog-to-digital converter 62, and then to manipulate this data in a predetermined fashion to produce an output data stream which is used as the basis for the visual display of the systolic and diastolic blood pressure readings. This data stream appears on lines 350 and 352.

With reference to FIG. 7, the data stream of lines 350 is fed to a BCD-to-7-segment latch decoder driver 320. The output of the driver 320 is fed via lines 322 to a group of six display devices 331. Each of the devices is capable of displaying a number between "0" and "9" in response to the signal received from the driver 320. In addition, each one of the display devices is connected through a amplifier-inverter pair 326 to the output of a BCD-to-decimal decoder 324. The decoder 324 receives the data appearing on lines 352, and decodes this data to determine which of the display devices will actively display a number.

The display devices 331 are arranged to display both systolic and diastolic pressures at the same time. The systolic pressure is displayed by devices 328-1, 330-1, and 332-1, which present in eye readable form, the units digit, the tens digit, and the hundreds digit, respectively for the systolic reading. In like manner, the diastolic reading in units, tens and hundreds is provided by devices 328-2, 330-2, and 332-2, respectively.

In arriving at the visual display of systolic and diastolic pressure readings on display 52, the microcomputer 50 produces signals which control the operation of the other elements in the blood pressure system. The microcomputer 50 produces a signal "B" on line 310 after passing through inverter 309, and a signal "A" on line 292. These two signals are used to control the inflate/deflate controller 72, which was discussed in detail hereinbefore.

At appropriate times, the microcomputer 50 also produces additional control signals such as the BAND PASS signal produced on line 186 which is used to selectively control the bandpass filter 172 forming part of the K-sound detector 44 previously described in detail with reference to FIG. 2. Also, the microcomputer 50 produces a HI-GAIN signal, on line 154, which is used to control the gain control 152 that forms part of the sound sensor 150 as described in detail hereinbefore, again with reference to FIG. 2.

The microcomputer 50 also produces a series of control signals which are received by the function indicator 51. With reference to FIG. 6, the function indicator contains four devices such as light emitting diodes 312-1 through 312-4 each of which is connected between the plus terminal of the battery 94 and ground, through a series arrangement of a resistor R70 and a switching transistor T10. Each switching transistor T10 has its emitter connected to ground and its collector connected to one side of the light emitting device via resistor R70. The base of each transistor T10 receives one of the function control signals appearing on lines 354 through 357. The signal on line 354 causes device 312-1 to light thus indicating that the user should re-apply the cuff. The signal on line 355 causes device 312-2 to light indicating that the blood pressure instrument has gone into the mode where the cuff pressure is being increased. The signal on line 356 causes device 312-3 to light thus indicating that the blood pressure instrument is in the inflation mode. Finally, the signal on line 357 causes the device 312-4 to light thus indicating that a blood pressure reading comprising both systolic and diastolic pressures has been made.

Pulse Transfer System

As previously stated, with reference to FIG. 1 of the drawings, the PPM 112 is connected to the blood pressure instrument 10 via induction coils 115 (made up of individual coil 116 contained in the blood pressure instrument 10 and individual coil 114 contained in the PPM unit 112). As also stated previously, and as will be seen in detail below, induction coils 115 serve the dual purposes of transmitting charging power from the blood pressure instrument 10 to the PPM 112 for charging the batteries thereof, and of transmitting pulsatile information or data from the blood pressure instrument 10 to the PPM unit 112 so as to permit the latter to perform calculations necessary for display of pulse information.

Further referring to FIG. 1 of the drawings, blood pressure instrument 10 has a dedicated controller 50 which provides a control output, via line 118 and inverter 120, as input PULSE to driver 122. This control input causes driver 122 to control oscillator 124, as will now be explained in detail.

Figure 8:
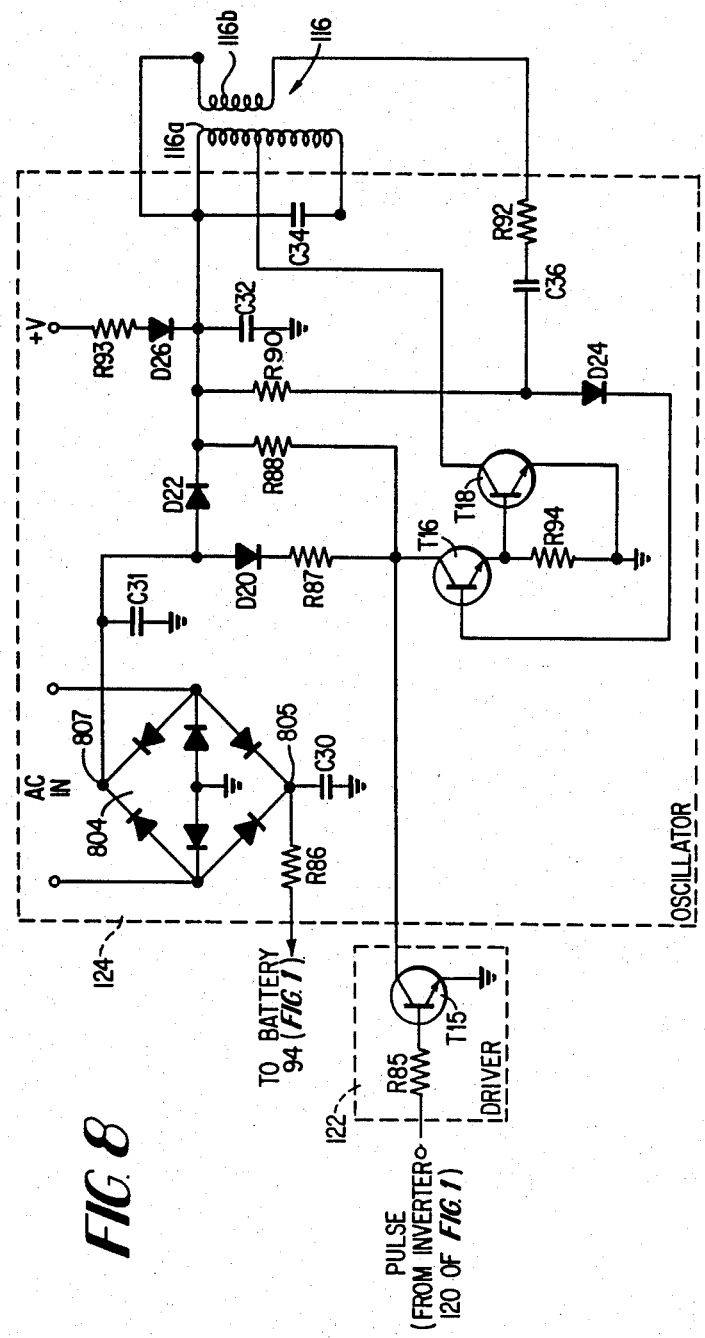
FIG. 8 is a schematic diagram of an embodiment for a driver and an oscillator for use in the pulse transfer function.

FIG. 8 is a detailed schematic of the driver 122 and oscillator 124 of FIG. 1.

Driver 122 comprises a resistor R85 and NPN transistor T15 connected in series.

Oscillator 124 comprises a diode bridge 804 having two opposing terminals for receiving A.C. power input, a third terminal 805 connected via capacitor C30 to ground, and a further terminal 807 for providing an output. Terminal 805 of bridge 804 is connected via resistor R86 to battery 92 (FIG. 1).

The output terminal 807 of bridge 804 is connected as follows: via capacitor C31 to ground; via diode D20 and resistor R87 to the collector of NPN transistor T16; via diode D22 and resistor R88 to the collector of transistor T16; via diode D22, resistor R90 and diode D24 to the base of transistor T16; via diode D22 and capacitor C32 to ground; and via diode D22 to one end of coil portion 116a (of coil 116 of FIG. 1), the other end of which is connected via capacitor C34 and diode D22 to output terminal 807 of bridge 804. Output terminal 807 is further connected via diode D22 to one end of coil portion 116b (of coil 116), the other end of which is connected via resistor R92, capacitor C36 and diode D24 to the base of transistor T16. The junction between capacitor C36 and diode D24 is connected to output terminal 807 via resistor R90 and diode D22. A positive voltage power supply is connected via resistor R93 and diode D26 to the junction between diode D22 and capacitor C32.

Oscillator 124 further includes NPN transistor T18 which has its base connected to the emitter of transistor T16, its collector connected to a mid-tap of coil portion 116a, and its emitter connected to ground, the base and emitter of transistor T18 being connected via feedback resistor R94.

Figure 9:
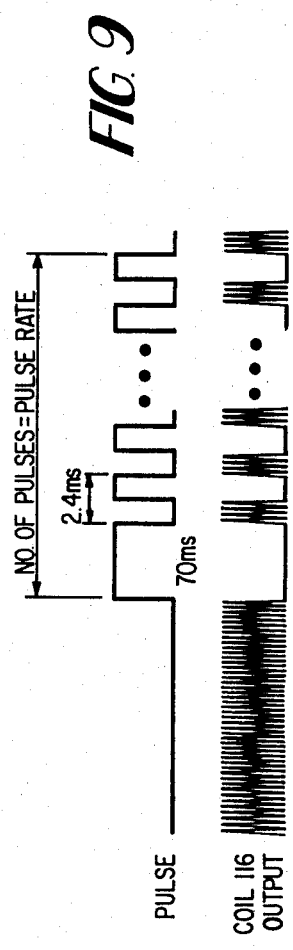
FIG. 9 is a timing diagram used to explain the pulse transfer function.

In operation, driver 122 receives control signal PULSE from dedicated controller 50 of FIG. 1, PULSE having a waveform as represented in FIG. 9. That is, controller 50 of FIG. 1 generates waveform PULSE having a logic one value of predetermined duration (preferably, 70 milliseconds), followed by alternate zero and one values occuring within a given cycle (preferably, 2.4 milliseconds). Thus, controller 50 generates a number of pulses (for example, 80 pulses): a first logic one value or pulse of longer duration, followed by a series of logic one values or pulses of shorter duration, the number of pulses equaling the pulse rate of the patient being examined.

Referring to FIG. 8, when PULSE has a logic zero value, transistor T15 is turned off, and oscillator 124 runs on "feedback." That is to say, when transistor T15 is off, a positive bias voltage +V is applied via resistor R93, diode D26, and resistor R88 to the collector of transistor T16, causing conduction thereof. As a result, a further bias is applied to the base of transistor T18, causing that transistor to conduct as well. With transistors T16 and T18 turned on, oscillator 124 is permitted to run on feedback via coil portion 116b, resistor R92, capacitor C36, and diode D24 connected to the base of transistor T16. This results in generation, by coil 116, of the oscillatory output shown in FIG. 9.

Conversely, when PULSE is logic one, transistor T15 in driver 122 is turned on, and the positive bias previously applied to the collector of transistor T16 is shunted away. As a result, transistor T16 is non-conductive, resulting in lack of a bias voltge applied to the base of transistor T18, which accordingly also does not conduct. As a result of transistors T16 and T18 being non-conductive, oscillator 124 ceases to generate an oscillatory output waveform, as represented in FIG. 9 by the zero output (for example, during the 70 milliseconds during which PULSE is logic one).

As further shown in FIG. 9, controller 50 of FIG. 1, via its control output PULSE, controls oscillator 124 via driver 122 so as to result in alternate oscillatory waveform outputs from the coil 116.

It is to be noted that oscillator 124 is provided with A.C. power input terminals (AC IN) by means of which A.C. power is provided via diode bridge 804 to the remainder of the oscillator 124. The A.C. power provided to diode bridge 804 charges battery 94 via charging resistor R86. Moreover, the A.C. power input to diode bridge 804 results in generation of a full amplitude waveform (coil 116 output of FIG. 9) during periods of PULSE equal logic one, which full amplitude waveform is transmitted via coil 116 and coil 114 (FIG. 1) to the PPM unit 112 for the purpose of recharging the battery thereof.

Conversely, when the blood pressure instrument 10 is disconnected from the A.C. power source, A.C. power is no longer provided to the oscillator 124 or to the PPM unit 112 (FIG. 1). Nevertheless, the coil 116 of oscillator 124 is still able to produce a coil 116 output of approximately half amplitude, so that pulsatile information can still be transmitted via coil system 110 (FIG. 1) to the PPM unit 112, even though recharging of batteries in blood pressure instrument 10 and PPM unit 112 does not take place.

Figure 10:
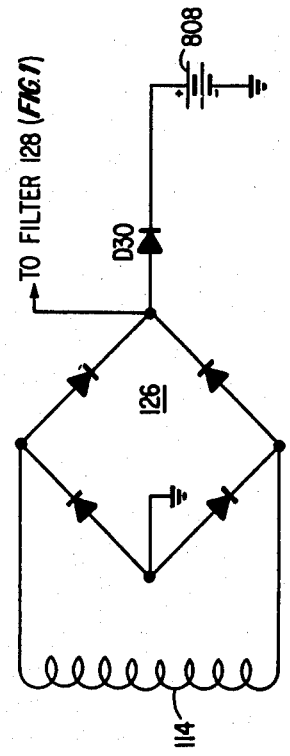
FIG. 10 is a schmatic diagram of a diode bridge for use in the pulse transfer function.
Figure 14:
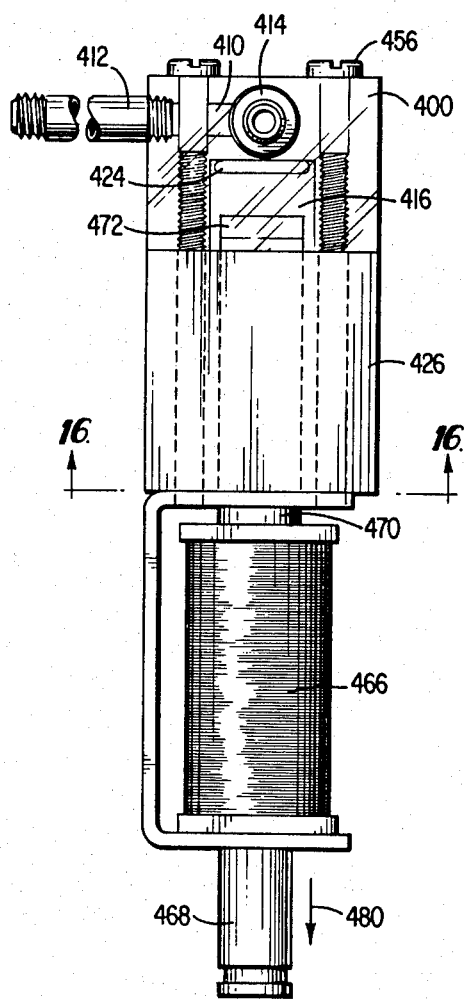
FIG. 14 is a plan view partially cut away of the solenoid valve assembly of FIG. 12.

FIG. 10 is a schematic diagram of a portion of the PPM unit 112 of FIG. 1. Specifically, PPM unit 112 includes a diode bridge 126 connected to coil 114, the output of diode bridge 126 being connected both to filter 128 and via diode D30 and resistor R95 to battery 808.

In operation, the output of coil 116 (as seen in FIG. 9) is received via coil 114, converted to a full wave output by diode bridge 126, and then provided both to filter 128 and battery 808. Thus, whenever PULSE equals logic one, pulsatile information is provided to the filter 128. Additionally, whenever the blood pressure instrument is connected to an A.C. power source, the signal received over coil 114 is, as previously explained, of sufficient amplitude (full amplitude waveform) to cause battery 808 to be recharged thereby.

Figure 11:
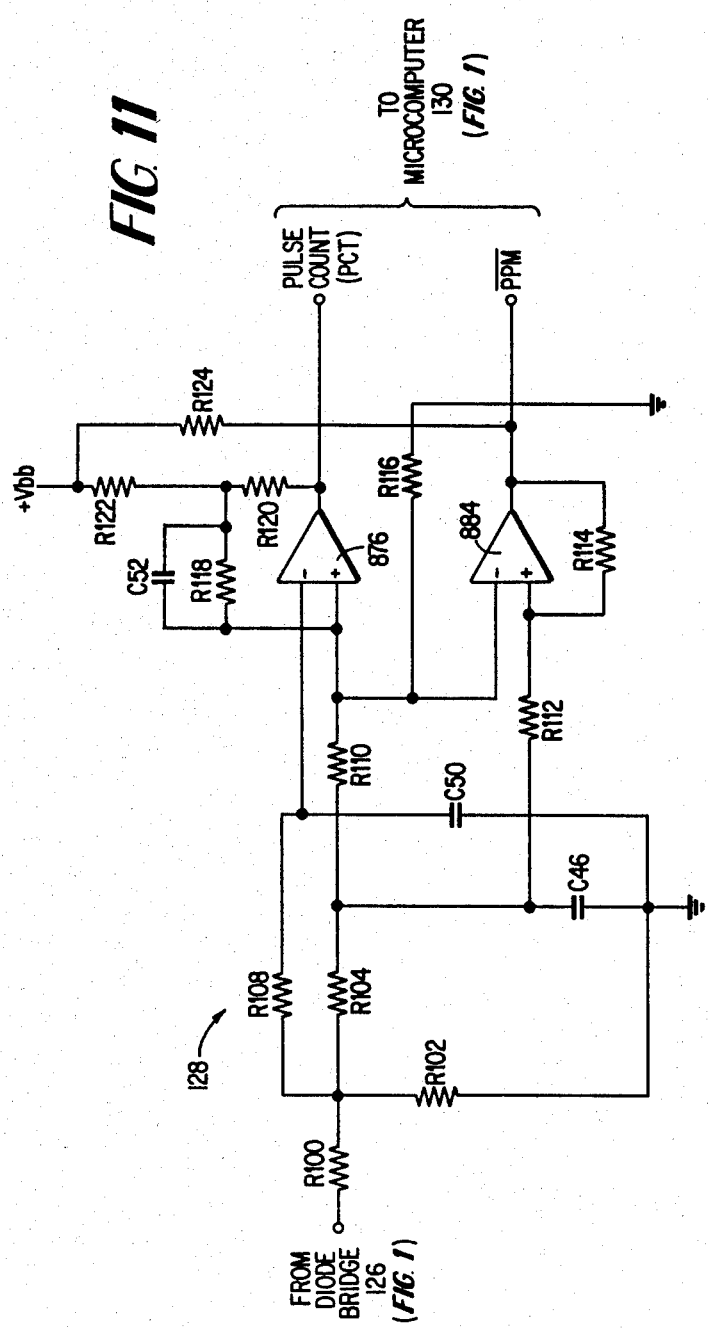
FIG. 11 is a schematic diagram of an embodiment for a filter as used in the pulse transfer function.

FIG. 11 is a schematic diagram of filter 128 of the PPM unit 112 of FIG. 1. Filter 128 comprises a voltage divider made up of resistors R100 and R102, a filter network made up of resistor R104 and capacitor C46, a further filter network make up of resistor R108 and capacitor C50, a further voltage divider (divide-by-two) made up of resistors R110 and R116, a comparator 876 having an associated hysteresis loop made up of resistors R120 and R118 and capacitor C52, and a further comparator 884 having an input resistor R112 and a feedback resistor R14. A supply voltage Vbb is connected via resistor R122 to the junction between resistors R120 and R118 associated with comparator 876, and further connected via resistor R124 to the output of comparator 884.

In operation, filter 128 receives the output of coil 114 as full-wave converted by diode bridge 126 (FIG. 10). The amplitude of the received signal is reduced by voltage-dividing resistors R100 and R102 (FIG. 11), and then filtered by resistor R104 in combination with capacitor C46, so that a steady-state D.C. output is provided at the junction between resistors R104 and R110. This steady-state output is then further voltage-divided by resistors R110 and R116 prior to provision to the positive input of comparator 876.

The same received signal, as voltage-divided by resistors R100 and R102, is filtered by resistor R108 in combination with capacitor C50, so as to result in an output which is an envelope of the received signal, such being provided to the negative input of comparator 876. Thus, comparator 876 compares the envelope of the received signal with a one-half voltage-divided, steady-state D.C. conversion of the received signal, and as a result generates output PULSE COUNT (PCT) which is a square pulse waveform with each square pulse corresponding to the square pulses shown in FIG. 9, as provided by inverter 120 of FIG. 1 to the driver 122. That is to say, comparator 876 and the associated circuitry discussed above convert the signal received by diode bridge 126 back to the original PULSE input to driver 122 in the blood pressure instrument 10 of FIG. 1.

Filter 128 further generates a digital output $\overline{PPM}$ as follows. The received signal, as voltage-divided by resistors R100 and R102, filtered by resistor R104 and capacitor C46, and voltage-divided by resistors R110 and R116, is provided to the negative input of comparator 884. Moreover, the received signal, as voltage-divided by resistors R100 and R102, and filtered by resistor R104 and capacitor C46, is provided via resistor R112 as a steady-state D.C. voltage input to the positive input of comparator 884. Thus, comparator 884 performs a comparison between a one-half voltage-divided steady-state input and a full steady-state input. So long as a signal (that is, an oscillatory waveform as shown in FIG. 9) is being received by the coil 114, diode bridge 126 and filter 128 of FIG. 8, the positive input to comparator 884 (FIG. 11) will be greater than the negative input thereto, resulting in generation of a logic one at $\overline{PPM}$. This indicates that the PPM unit 112 is mounted on (connected to) the blood pressure instrument 10 of FIG. 1, and that the pulse rate information may be calculated by the PPM unit 112 based on the pulsatile information received via the coils 114 and 116.

Conversely, when no signal is being received via coil 114 and diode 126 by the filter 128, bias voltage Vbb biases the negative input of comparator 884, resulting in the negative input of comparator 884 exceeding the positive input thereto, and comparator 884 produces a logic zero at output $\overline{PPM}$. This indicates that the PPM unit 112 is not mounted on (connected to) the blood pressure instrument 10, and that pulse rate information should be derived from means other than the blood pressure instrument 10 (for example, from a finger sensor device conventionally associated with the PPM unit 112).

Returning to consideration of FIG. 1, the PPM unit 112 is seen to include a microcomputer (or other computer device) 130 (FIG. 1) for computing pulse rate information based on the received pulsatile information transferred to the PPM unit 112 via the coil system 110, and then converted to pulse waveform PCT (corresponding to original pulse waveform PULSE provided by controller 50 of FIG. 1) by filter 128 of FIG. 11, as just described above. Microcomputer 130 also receives digital input $\overline{PPM}$ by means of which the status of the PPM 112 (connected or not connected to the blood pressure instrument 10) is indicated, thus indicating to microcomputer 130 whether or not the data PULSE (and corresponding data PCT) are to be used in calculating the pulse rate of the patient.

A flowchart of the operations performed by the microcomputer 130 in performing the latter calculations is described below. The pulse information, as computed by microcomputer 130, is displayed by conventional means represented by display unit 132 (FIG. 1).

System Operation

Figure 37:
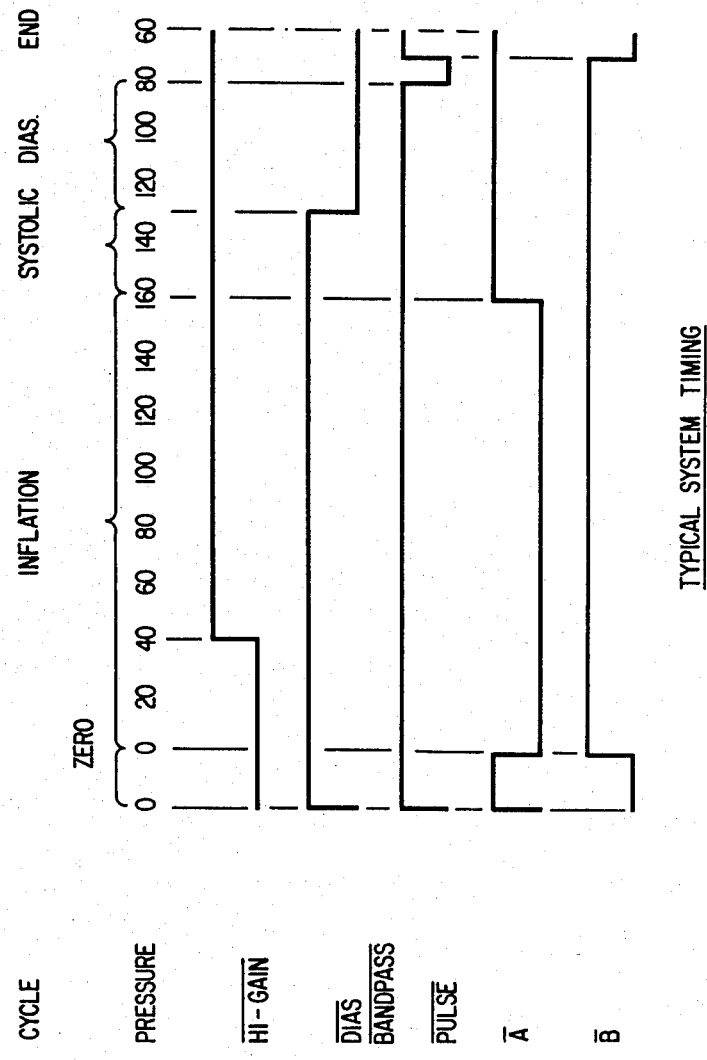
FIG. 37 is a typical timing diagram used in conjunction with a description of the system operation.

In order to carry out all of the operations described above, the microcomputer 50 generates certain output signals with particular system timing, as shown in FIG. 37 which is a timing diagram of such outputs. Moreover, the microcomputer 50 is programmed as a dedicated controller. Accordingly, FIGS. 38 through 45 are illustrative of a typical program, in accordance with which the microcomputer 50 is programmed. It is to be clearly understood that the program or programs illustrated by the flowcharts in FIGS. 38 through 45 are merely typical, and that other programs and modifications to those programs will readily become apparent to those skilled in the art.

Referring to FIG. 37, typical system timing for generation of output signals $\overline{HI\text{-}GAIN}$, $\overline{DIAS}$ (previously referred to as $\overline{BAND\ PASS}$), $\overline{PULSE}$, $\overline{A}$ and $\overline{B}$ is shown. Signal $\overline{HI\text{-}GAIN}$ changes state once the pressure rises above 40 mm. Hg., such signal being applied to the gain control 152 in sensing circuit 150 of FIG. 2 so as to compensate for abnormally low intensity K-sounds by increasing the magnitude of the signal received by the amplifier 46-2. Signal $\overline{DIAS}$ corresponds to signal $\overline{BAND\ PASS}$, and is on (or high) during the cycle of operation up to to the point where systolic measurement has been accomplished and diastolic measurement commences, at which time it goes off (or low). Signal $\overline{BAND\ PASS}$ is applied to band-pass filter 172 in K-sound detector 44 of FIG. 2, so that transition in signal $\overline{BAND\ PASS}$ causes selective change of the pass-band of the filter 172 in order to adapt the K-sound detector 44 for use in diastolic measurement. Signal $\overline{PULSE}$ is the signal provided by microcomputer 50 to inverter 120 of FIG. 1, wherein it is inverted prior to provision, via driver 122, oscillator 124 and induction coils 110 to the PPM unit 112. Signal $\overline{A}$ is off (or low) during the inflation cycle, but is on (or high) at all other times, and is provided to function selection circuit 290 in inflate/deflate controller 72 of FIG. 4 for the purpose of activating controller 72 to inflate blood pressure cuff 16 of FIG. 1 (inflation corresponding to signal $\overline{A}$ being low). It will be recalled that signal $\overline{A}$ is also provided via inverter 206 to resistor network 204 of FIG. 2 so as to adjust the level of threshold voltage received by comparator 182 in accordance with the selected mode of operation (inflation or deflation) of the blood pressure instrument. That is to say, initially $\overline{A}$ is high (during the auto zero period) but goes low during the inflation cycle so as to raise the threshold of the reference input of comparator 182; subsequently, during deflation (at the commencement of the systolic period), $\overline{A}$ goes high, thus lowering the threshold of the reference input to comparator 182. Finally, signal $\overline{B}$ is generated by microcomputer 50 during the inflation, systolic, and diastolic periods of the cycle of operation of the blood pressure instrument, signal B being applied (it will be recalled, referring to FIG. 4) to the error amplifier 264 contained within control circuit 250 of inflate/deflate controller 72.

Figure 44:
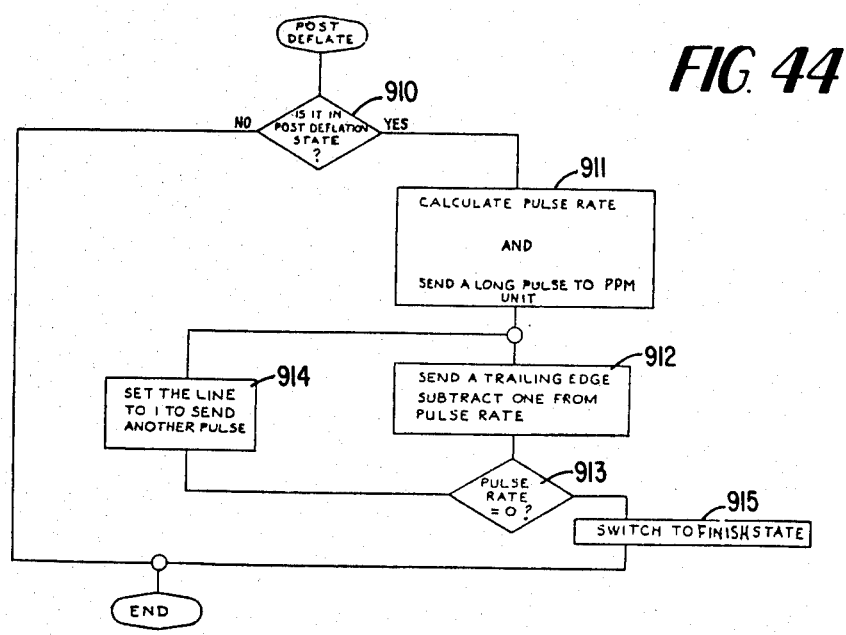

Generation of the aforementioned signals by microcomputer 50 is achieved under program control, microcomputer 50 consecutively (in loop-like fashion) executing the following routines in sequence: auto zero routine (FIG. 38), signal processing routine (FIG. 39), pulse count routine (FIG. 40), inflate routine (FIG. 41), post inflate routine (FIG. 42), deflate routine (FIGS. 43A and 43B), and post deflate routine (FIG. 44). In addition, microcomputer 50 executes a timer interrupt routine (FIG. 45) which serves to continually manage the various timers employed by microcomputer 50 in executing the various previously mentioned routines. Prior to discussing each flowchart individually, it should be recognized that decision blocks (represented by diamonds in the figures) are arranged such that, unless otherwise specified, a "yes" answer to the question is represented by a rightward branch from the decision block and a "no" answer is represented by a leftward branch from the decision block.

Figure 38:
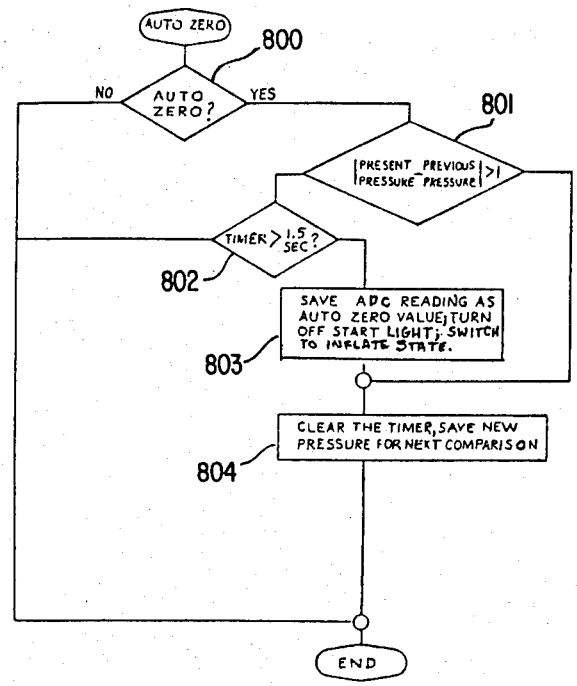
FIGS. 38 through 42, 43a, 43b, and 44 through 46 are flow charts of operations performed by the microcomputers in the blood pressure system and the physiological parameter measuring device.

FIG. 38 is a flowchart of the auto zero routine continually performed by the microcomputer 50 in order to compensate for an offset voltage in the analog signal representing measured pressure, as measured via pressure transducer 54 (FIG. 1), amplifier 60 and analog-to-digital converter 62. In accordance with the routine, a comparison of present pressure versus previous pressure is performed (block 801). Referring to blocks 802–804, if the present pressure differs from the previous pressure by greater than 1 mm. Hg., the timer is cleared and the new pressure is saved for the next comparison; if the present pressure and previous pressure do not differ by more than 1 mm. Hg., and if the timer shows greater than 1.5 seconds, the present pressure reading of the analog-to-digital converter 62 (FIG. 1) is saved as the auto zero value, a start light (located on the face of the blood pressure instrument) is turned off, and microcomputer 50 switches to the inflate state; conversely, if the present and previous pressure do not differ by more than 1, and if the timer doen not show more than 1.5 seconds, the auto zero routine is ended.

Figure 39:
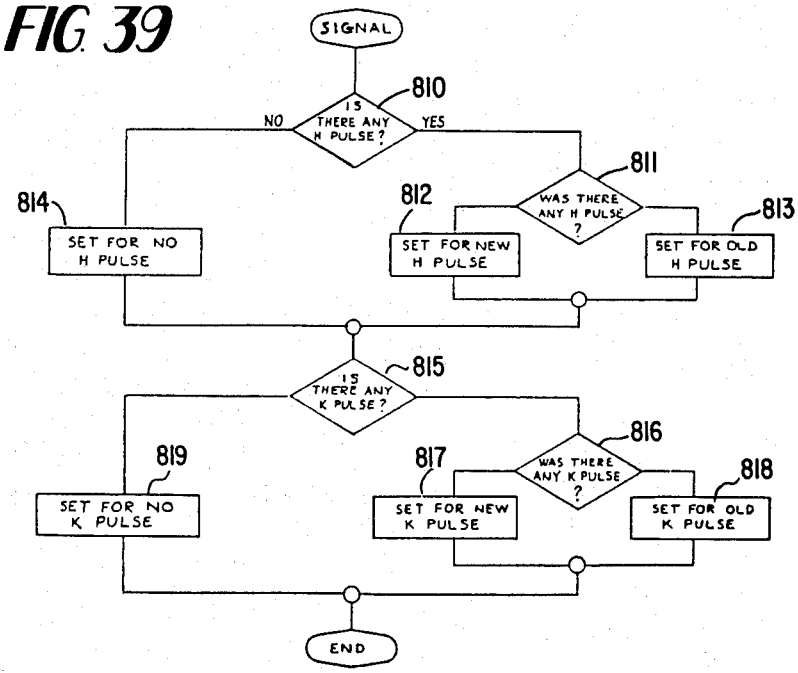

FIG. 39 is a flowchart of the signal processing routine executed by microcomputer 50. Blocks 810–813 represent a series of steps for identifying incoming H (heartbeat) pulses, while blocks 815–818 represent a series of steps for identifying incoming K (K-sound) pulses. In accordance with the represented steps, microcomputer 50 sets various flags to indicate the results of the signal processing routine: no H pulse, old H pulse, new H pulse, no K pulse, old K pulse and new K pulse.

Figure 40:
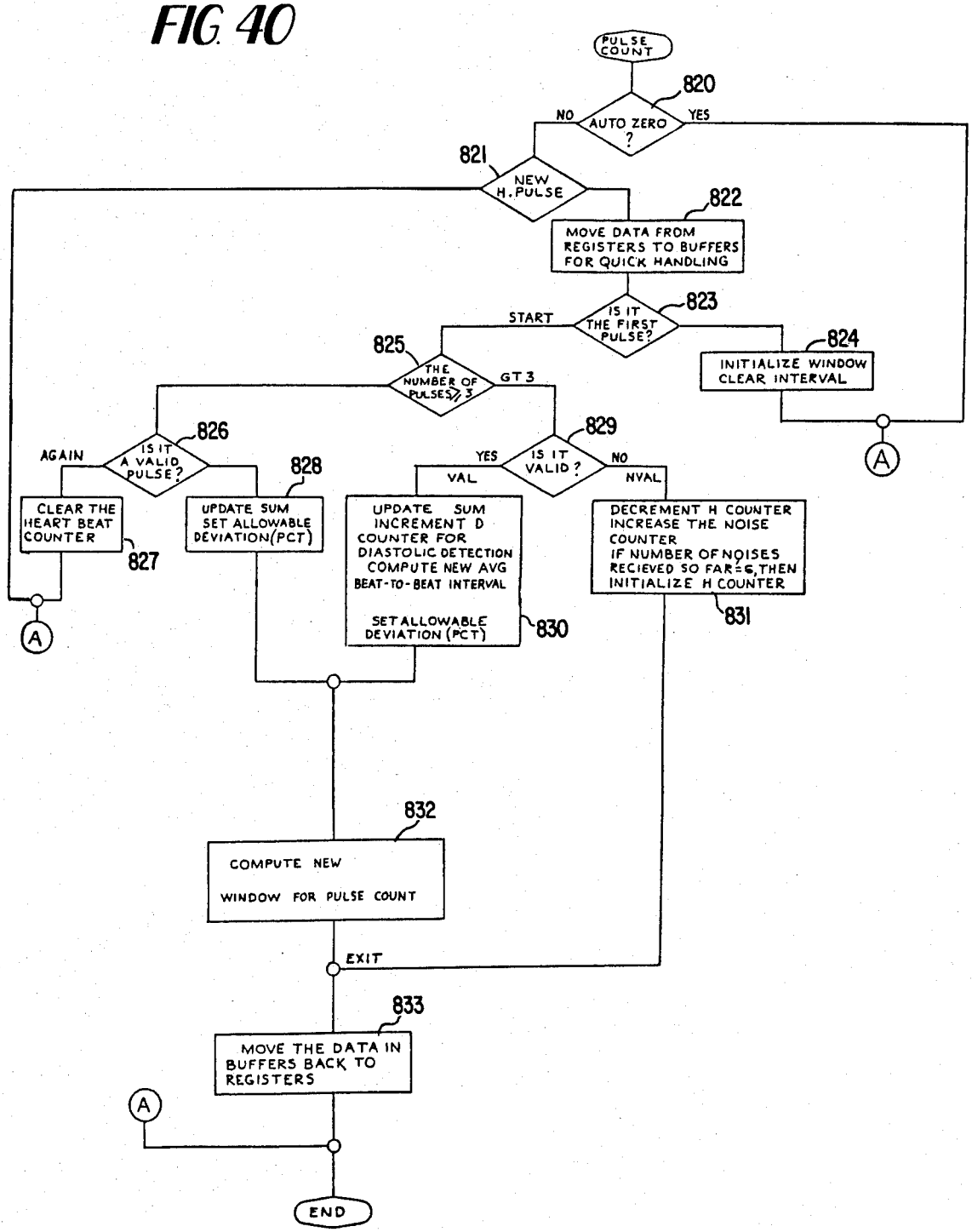

FIG. 40 is a flowchart of the pulse count routine executed by microcomputer 50. Referring to block 820, it is noted that, prior to entering the pulse count routine, a check is made as to whether or not the auto zero routine is indicated. If auto zero routine is indicated, a branch to the end of the pulse count routine is executed, and the microcomputer 50 then executes the auto zero routine in accordance with the steps represented by the flowchart of FIG. 38. If auto zero routine is not indicated, a check as to H pulse identification (no pulse, new pulse, old pulse as previously discussed) is accomplished, and if a new H pulse is not indicated, the pulse count routine is then ended. Conversely, if a new H pulse is indicated, data (developed by previous execution of the pulse count routine) is moved from registers to buffers for high speed handling, and the procedure continues. If the H pulse is a first pulse (block 823), an initial "window" (for excluding noise from the received pulse count information) is set (block 824), and the pulse count routine is ended. If the pulse is not a first pulse, the routine then makes a decision (block 825) as to whether or not the pulses re greater than three in number. If greater than three, a data validity check (block 829) is performed (that is, a determination of whether or not the pulse is within the "window" previously set is made). If the data is invalid, the H counter is decremented (representing discarding of the present pulse), a noise counter is incremented (representing reception of noise or invalid data), and then, if the number of noise signals received thus far equals six, the H counter is initialized (signifying complete restarting of the pulse counting procedure), and an exit from the routine is made via block 833. On the other hand, if the number of pulses is greater than three (block 825), and the data is judged to be valid (block 829), the sum of beat-to-beat intervals between H pulses is updated, a D counter (utilized for diastolic detection) is incremented, a new average value for beat-to-beat interval is computed, and an allowable deviation (PCT), related to "window" size, is set. Then, referring to block 832, a new "window" for pulse counting is computed, and the routine is ended via block 833. Returning to block 825, if the number of pulses is not greater than three, and a valid pulse is not received (block 826), the H counter is cleared, the routine is ended, and the pulse counting procedure must begin anew; conversely, if a valid pulse is received, the sum of the beat-to-beat intervals is updated and the allowable deviation (PCT) is set (block 828), a new "window" is computed (block 832), and the routine is ended via block 833.

To summarize the results achieved by the pulse count routine, reception of the first pulse initializes the "window" and clears an interval counter (block 824); reception of successive valid pulses, up to a total of three valid pulses, results in calculation of a sum of beat-to-beat intervals, as well as adjustment of the "window" based on an allowable deviation (PCT); then, upon reception of a total of at least three valid pulses, the sum of beat-to-beat intervals is updated, the diastolic counter is incremented, and a new average beat-to-beat interval is computed (which is subsequently used for "window" size adjustment). Moreover, eventually, the pulse rate (the inverse of pulse duration) is computed by dividing the sum of the beat-to-beat intervals by the number of pulses, subtracting one, and inverting the result (that is, inverting the average pulse duration) to get pulse rate. In addition, it is to be noted that the "window" size is modified as time goes on in accordance with the received data, with more weight being given to later received pulses; this compensates for the fact that the pulse rate of individuals changes during measurement thereof.

Figure 41:
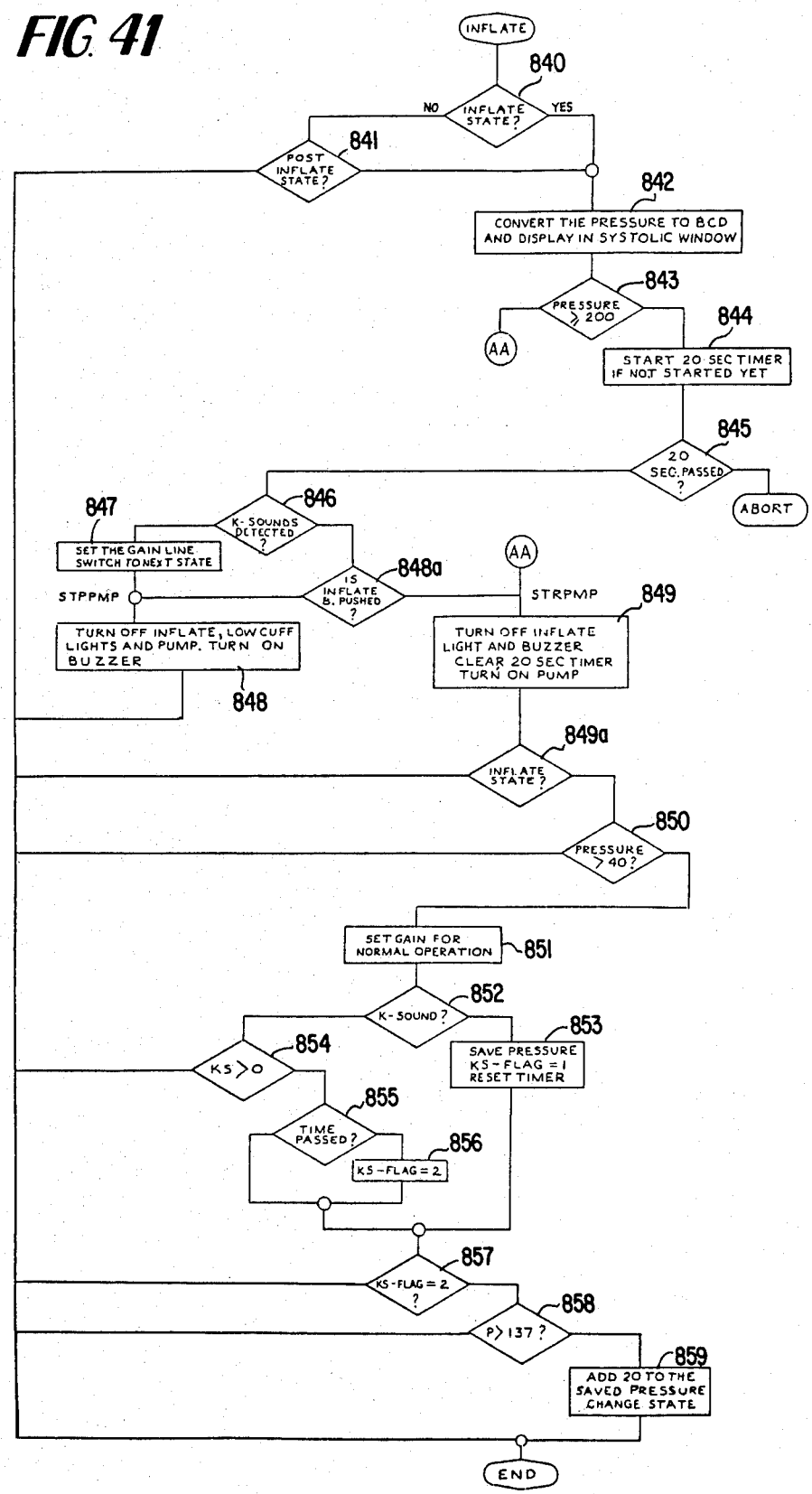

FIG. 41 is a flowchart of the inflate routine performed by microcomputer 50. As indicated by blocks 840 and 841, it is performed only when the microcomputer 50 is in the inflate or post-inflate states. In that eventuality, the pressure measured by pressure transducer 54 (FIG. 1), as provided by converter 62 to microcomputer 50, is converted to binary coded decimal (BCD) and displayed by the blood pressure instrument. It is to be noted that, since the inflate routine is cyclically executed (with various other routines) during the inflate (or post inflate) state of operation of the microcomputer 50, a continually changing (dynamic) display of systolic pressure is achieved. During the initial portion of the inflation cycle, the pressure is less than 200 (block 843), and accordingly the inflate light and buzzer are off, a 20 second timer (in microcomputer 50) is cleared, and the pump (for inflating) is turned on (block 849). When not in the inflate state (for example, when in the post-inflate state), the routine is ended (block 849a); conversely, when in the inflate state, and pressure is less than 40 (block 850), the routine is ended, while when pressure is greater than 40, the gain control 152 (FIG. 2) is set for normal operation (block 851) via signal HI-GAIN (discussed above). Referring to block 852, when K-sound is detected, the measured pressure is saved (for subsequent display per block 842 above), a KS-flag is set to one, a 1.25 second timer is set, and the routine is exited via decision block 857. Conversely, when K-sound is no longer detected (block 852), when KS-flag is greater than zero (block 854), and when 1.25 seconds has not past (block 855), the routine is again exited via block 857. However, when 1.25 seconds without a K-sound has past (1.25 seconds represents the expected time between K-sounds in a human being), the KS-flag is set to two, and a branch to block 858 is made via block 857. So long as pressure is equal to or less than 137, the routine is exited; however, when a pressure of 137 is reached, 20 is added to the saved pressure, state is changed to the post-inflate state, and the routine is ended.

Figure 42:
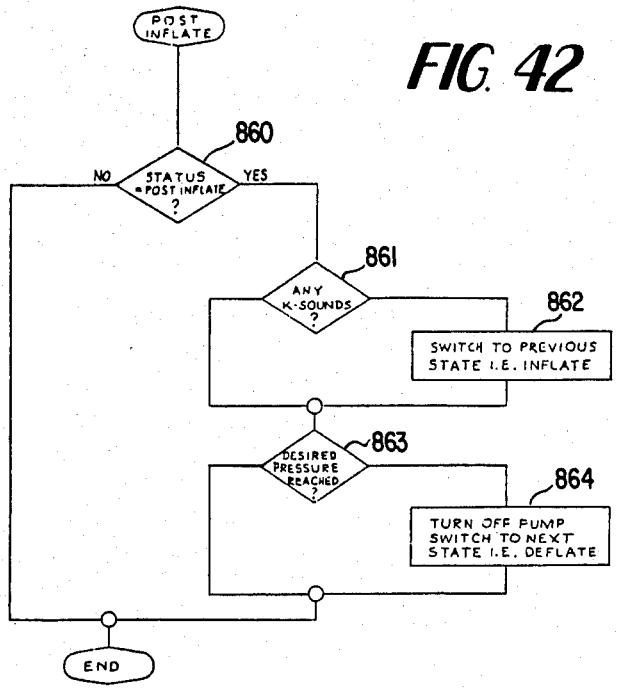

FIG. 42 is a flowchart of the post-inflate routine. When K-sounds are not detected (block 861), and the desired pressure is not reached (block 863), the routine is exited, thus permitting subsequent execution of the inflate state to achieve the desired pressure. If, in the post-inflate state, K-sounds are detected (block 861), a switch to the previous (inflate) state is indicated (block 862). Moreover, when the desired pressure is reached (block 863), the microcomputer 50 commands turn-off of the pump, and a transfer to the next state, the deflate state, is executed (block 864). It is to be noted that, at this juncture, the microcomputer 50 raises signal $\overline{A}$ to a logic one or high value, thus signifying entry of the deflate mode, and specifically the systolic portion of the operational cycle of the blood pressure instrument.

Figure 43A:
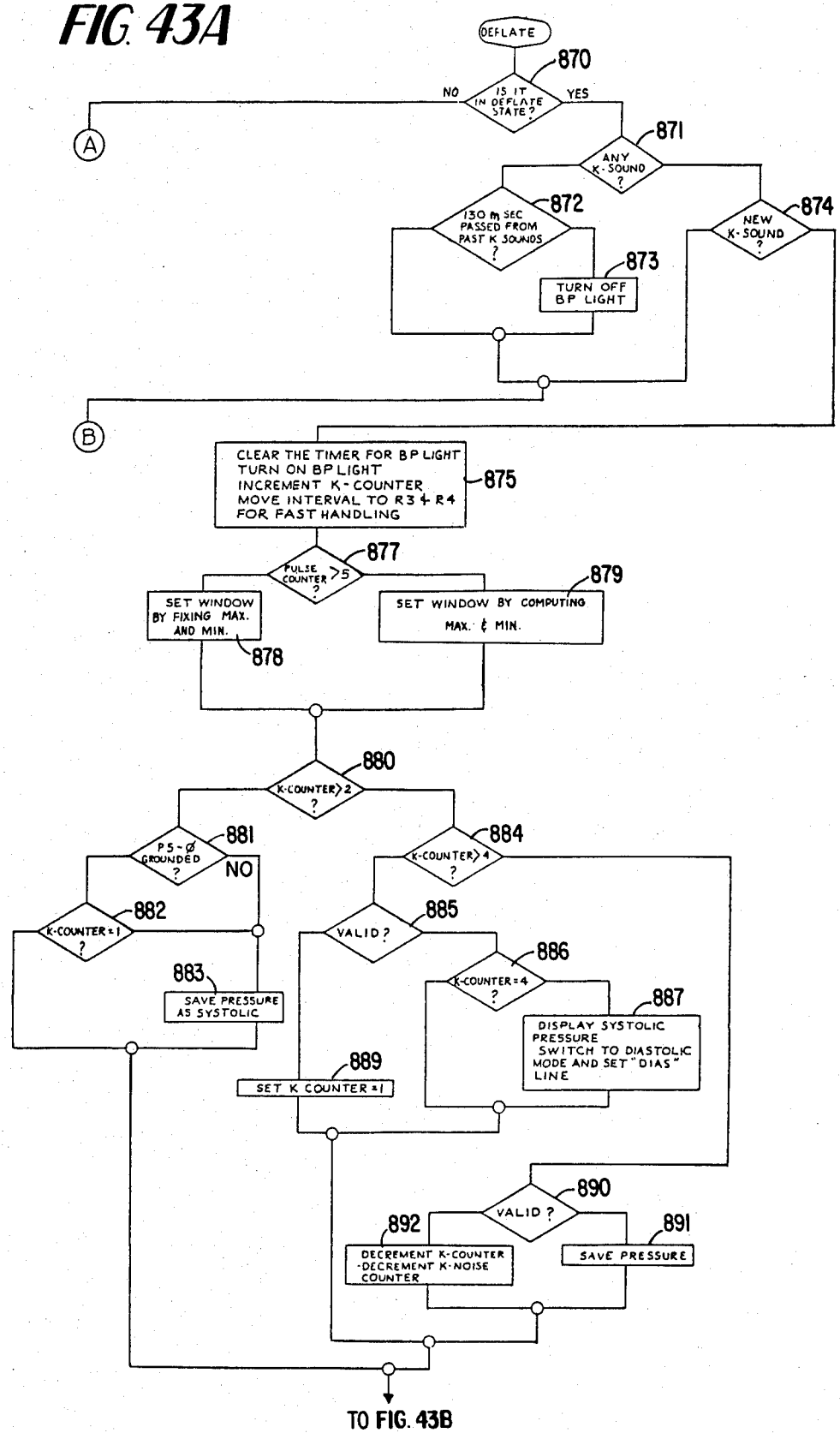
Figure 43B:
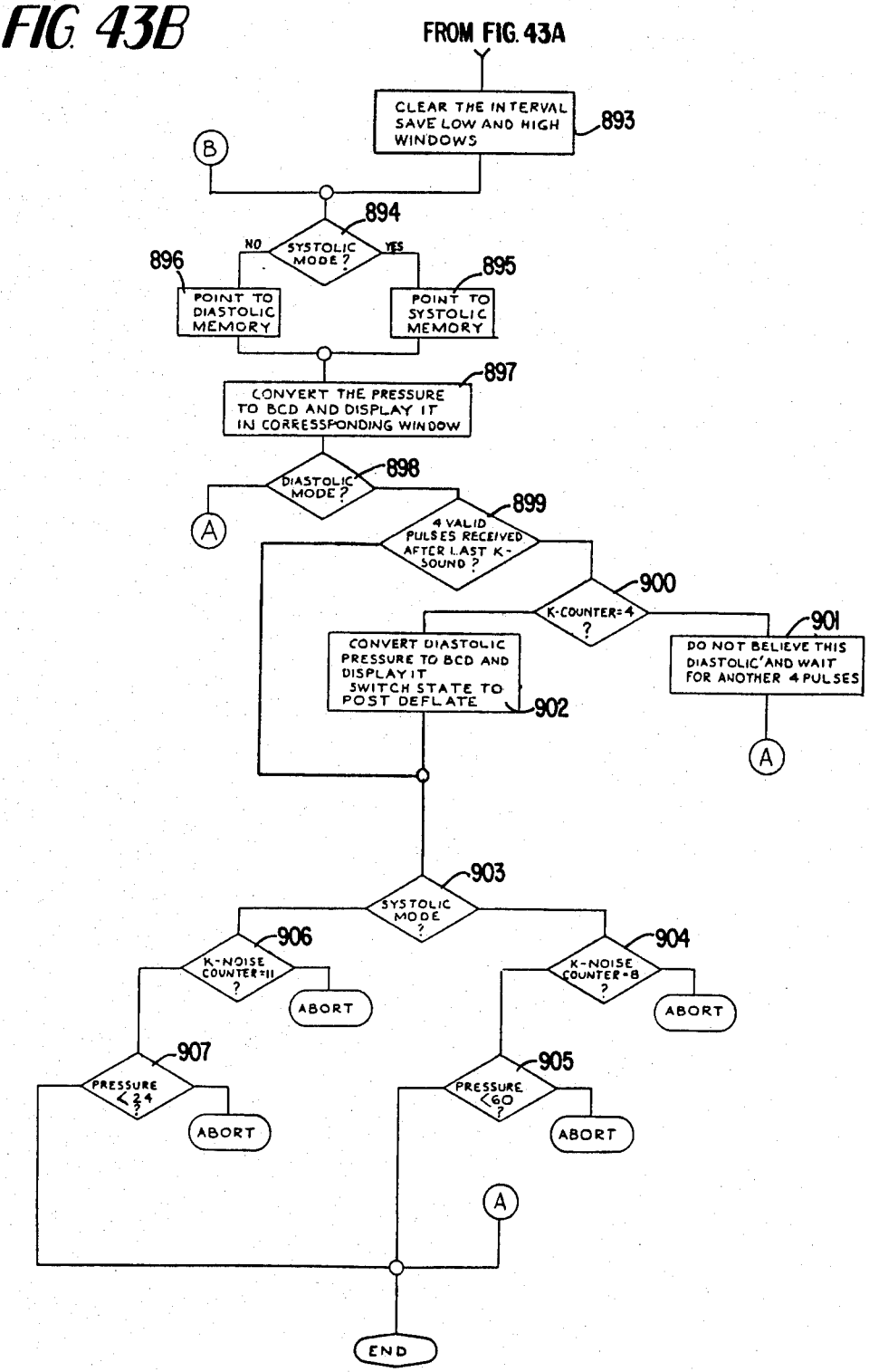

FIGS. 43A and 43B constitute a flowchart of the deflate routine executed by microcomputer 50. When in the deflate state (block 870), and when a K-sound is not detected (block 871), a 130-millisecond timer measures the time of absence of a K-sound (block 872). So long as 130 milliseconds does not pass, a branch to decision block 894 is executed, and since the systolic mode is initially being executed in the deflate cycle, a pointer to the systolic memory is set (blocks 894 and 895), the pressure is converted to BCD and displayed (block 897), and the routine is exited via block 898. If 130 milliseconds from the last K-sound passes (block 872), the BP instrument light is turned off (block 873), and blocks 894, 895, 897 and 898 are again executed, and the routine is ended. Conversely, when a K-sound is detected (block 871), a determination as to whether or not it is a new K-sound is made (block 874). Detection of an old K-sound results in a branch to blocks 894, 895, 897 and 898, and the routine is ended. Detection of a new K-sound results in execution of block 875, by which the timer for the blood pressure instrument light is cleared, and the light is turned on, resulting in enablement of a flashing light on the console of the blood pressure instrument (each flash of light indicating the reception of a K-sound). Further referring to block 875, the K-counter is incremented, the data INTERVAL (referring to beat-to-beat interval between K-sounds) is moved to microcomputer interval registers R3 and R4 (for fast handling), and the procedure continues as follows.

Referring to block 877, the blood pressure instrument is specially designed so that reception of a first K-sound before less than five pulses (heartbeats) have been counted results in a determination that the data is unreliable. As a result, the K-sound detection "window" is set by fixing it to certain maximum and minimum values. Conversely, if the first K-sound is detected after counting of five pulses, a determination that the data is reliable results, and the K-sound detection "window" is set by computing new maximum and minimum values therefor based on the received data. Thus, it is to be recognized that, as was the case with H-pulse detection, microcomputer 50 of the blood pressure instrument modifies or adapts the "window" for K-sound detection as time passes based on data received over that period of time.

Referring to blocks 880 through 882, the blood pressure instrument is so designed that a reading of systolic pressure can be made after reception of either the first K-sound or the second K-sound. This alternative capability is provided by selectively grounding or not grounding a particular terminal (designated P5-∅). When this terminal is grounded, a K-count of two will result in saving of the systolic pressure, while non-gounding of this terminal will result in saving of systolic pressure on a K-count of one. If the K-counter is zero, the routine branches to block 894, and the routine is exited via blocks 894 through 898.

In the event that the systolic pressure is saved (block 883), upon the obtaining of a K-count of greater than two (block 880), a further determination as to whether or not K-count is greater than four is made (block 884). If not greater than four, and if the data is invalid (block 885), the K-counter is set to one, the data INTERVAL is cleared and the low and high "window" data is saved (block 893), and the routine is ended via blocks 894 through 898. On the other hand, if the K-count is not greater than four, but the data is valid (block 885), a K-count of less than four will cause a branch to block 893 and exiting of the routine via blocks 894 through 898; if K-count equals four, that is, after the reception of four K-sounds, the systolic pressure (saved in block 883 during a previous execution of the routine) will be displayed, the diastolic mode of operation will be entered, and the signal DIAS (also referred to as BAND PASS) will go high (see timing diagram of FIG. 37 which shows $\overline{\text{DIAS}}$ or $\overline{\text{BAND PASS}}$). As previously noted, signal $\overline{\text{BAND PASS}}$ is applied to comparator 182 in K-sound detector 44 of FIG. 2, and $\overline{\text{BAND PASS}}$ going low results in establishment of a lower threshold reference input to the comparator 182, thus adapting the comparator 182 for K-sound detection during the diastolic mode of operation. In addition, high pass filter 172 in K-sound detector 44 of FIG. 2 is varied (as to its band-pass characteristics) by this variation of signal $\overline{\text{BAND PASS}}$; that is, $\overline{\text{BAND PASS}}$ going low at the beginning of the diastolic period of operation results in reduction of the pass band of band-pass filter 172 from 20-100 Hz. (the systolic pass band) to 40-100 Hz. (the diastolic pass band).

Referring to FIGS. 43A and 43B, the deflate routine is successively and continually executed by microcomputer 50 as the deflation operation continues in the diastolic period. Referring to block 894 in FIG. 43B, pressure readings provided to the microcomputer 50 are stored in a diastolic memory (see block 896), and a dynamic display of the diastolic pressure is achieved by conversion to BCD (see block 897). It is to be noted that separate displays for systolic and diastolic pressures, respectively, are provided in the blood pressure instrument, and that, once the diastolic period commences (block 887 of FIG. 43A), the display of systolic pressure is "frozen."

Returning to FIG. 43B, blocks 898 through 907 describe the routine as executed in the diastolic mode. So long as four valid pulses are not received after the last K-sound (block 899), and so long as the K-noise counter does not equal or exceed 11, and so long as pressure remains equal to or greater than 24, the routine will be exited via blocks 903, 906 and 907. If four valid pulses are not received after the last K-sound, and either the K-noise counter achieves a value of 11 or the pressure falls below 24, measurement of the diastolic pressure will be aborted (see blocks 906 and 907). Once four valid pulses are received after the last K-sound, however, a check of the K-counter is made (block 900). If the K-counter reads four, the diastolic measurement is deemed to be unreliable, and another four valid H-pulses (after the last K-sound) will be awaited (block 901). If the K-counter does not equal four (block 900), the diastolic pressure will be converted to BCD, the diastolic display will be "frozen" at its current reading, and the microcomputer 50 will be switched to the post-deflate state (block 902).

To summarize the deflation cycle, as just described with reference to FIGS. 43A and 43B, the blood pressure instrument utilizes the reception of four valid K-sounds to validate the pressure reading as constituting an accurate measurement of systolic pressure, and such reading is "frozen" in the systolic pressure display. Then, cessation of the K-sounds, followed by reception of four H-pulses, validates the pressure reading as constituting an accurate reading of diastolic pressure, and the pressure reading is "frozen" in the diastolic pressure display.

FIG. 44 is a flowchart of the post-deflate routine. In this routine (block 910), calculation of pulse rate (as previously described) takes place, and a long pulse (preferably, 7 milliseconds, as shown in FIG. 9) is transmitted to the PPM unit 112 of FIG. 1 (block 911 of FIG. 44). Blocks 912 through 914 constitute that portion of the post-deflate routine which is responsible for the subsequent generation of relatively shorter pulses (preferably, having a cycle time of 2.4 milliseconds), such subsequent pulses being transmitted until the pulse rate (which is down-counted in the process) achieves zero. At that juncture, the blood pressure instrument switches to the finish state.

Figure 45:
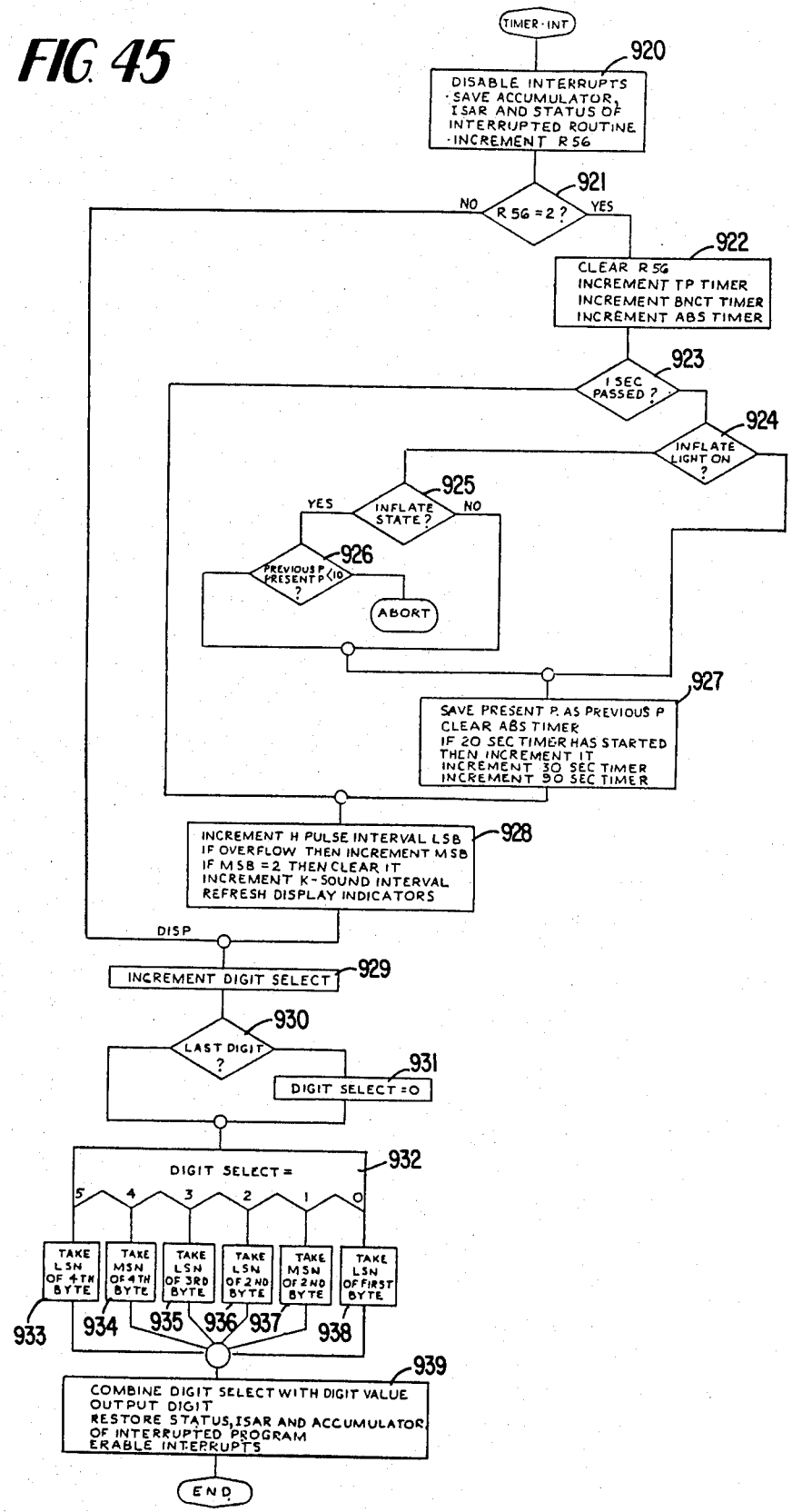

FIG. 45 is a flowchart of the timer-interrupt routine which the microcomputer 50 periodically enters for the purpose of management of various hardware timing devices located therein. Referring to block 920, upon entering this routine, the interrupts are disabled, the contents of various accumulator and status registers are saved, and a registerstored value R56 is incremented. Block 921 represents a decision as to whether or not R56 (which can take on the values of either one or two) is two in value. Thus, block 921 effectively achieves a branch through blocks 922 through 928 during every other pass through the timer-interrupt routine. When R56=2, the value thereof is set to zero (so that is may be incremented again in block 920 during the next execution of the routine), and various timers are incremented. Block 923 represents the operational characteristic by which a blood pressure measurement sample is taken every second. Thus, if one second has not passed, block 928 is executed; conversely, if one second has passed, and if the inflate light is on (block 924), block 927 is executed, followed by block 928; furthermore, if one second has passed, but the inflate ligh is off (blocks 923 and 924), a state check (block 925) is executed such that, if the inflate state is being executed, the previous and present pressure values are compared, and if a difference of less than 10 is determined, measurement by the instrument is aborted. If not in the inflate state (block 925), or if the difference between previous and present pressure measurements is equal to or greater than 10, block 927 is executed, followed by block 928.

Referring to block 929, this block and the subsequent blocks are executed on every pass through the timer-interrupt routine (see disccussion above relative to block 921 (R56=2?)). Once the digit select data, by which digits are selected for display, is incremented, block 930 questions whether or not the last digit is being displayed. If not, digit select block 932 is executed (depending on whether digit select=5, 4, . . . , 1, 0), followed by execution of block 939. If the last digit is being displayed, digit select is set to zero (blocks 930 and 931), and blocks 932 and 939 are then executed in sequence.

It is to be understood that the above constitutes just one embodiment for displaying data derived during execution of the previous routines, and that other display methods as would be known to one to one of ordinary skill in the art could as well be implemented.

Figure 46:
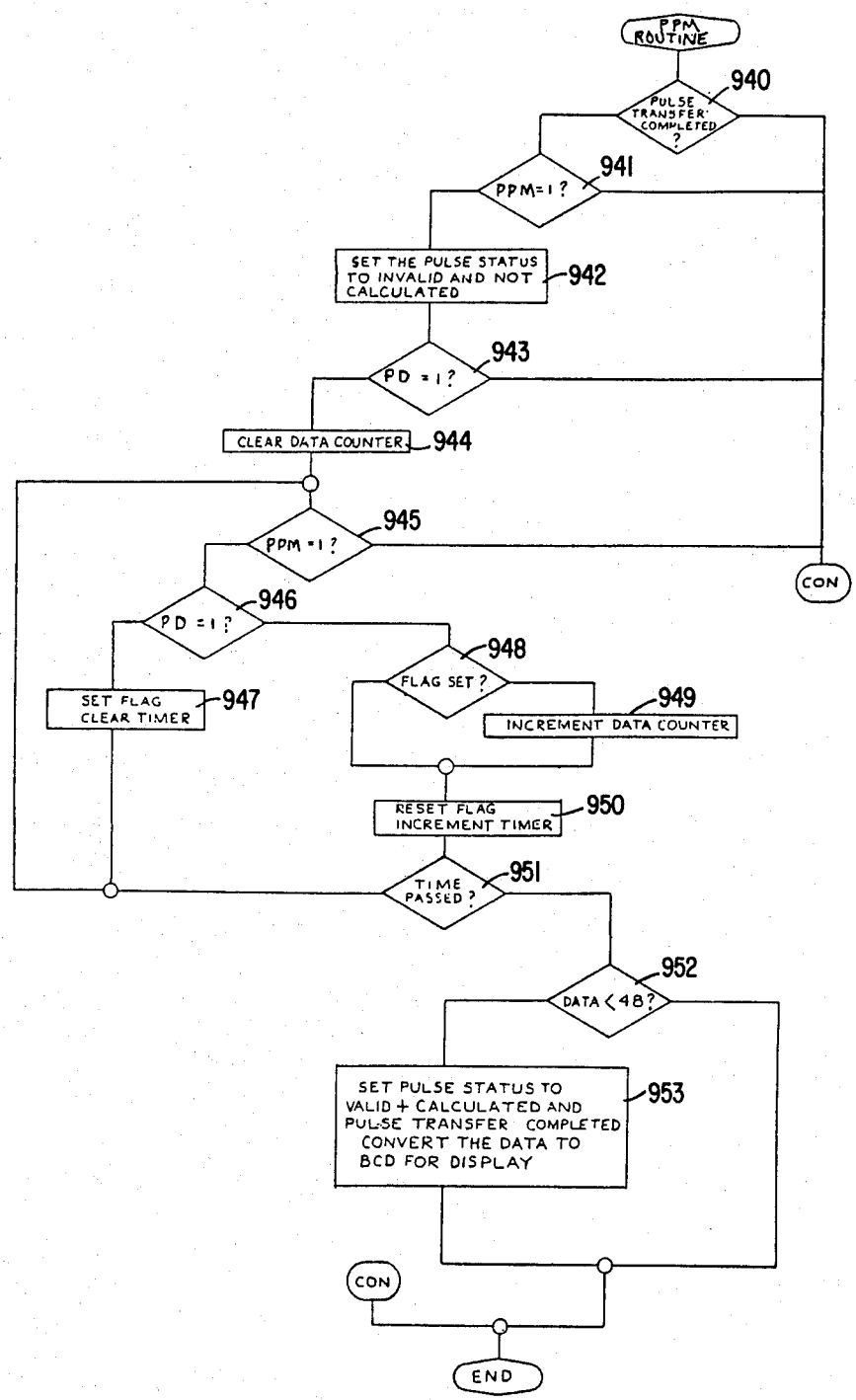

As mentioned previously in the detailed description of the PPM unit 112 (FIGS. 1 and 8-11 above ), PPM unit 112 includes a microcomputer 130 which is also, in the preferred embodiment, operated under program control. Accordingly, FIG. 46 is a flowchart of the PPM routine executed by microcomputer 130 of PPM unit 112.

Microcomputer 130 executes the PPM routine until a pulse transfer has been completed (as indicated by block 940). In accordance with block 941, the status of flag PPM is checked; PPM=1 when the PPM unti 112 is not connected to the blood pressure instrument 10 of FIG. 1 for pulse data reception, and PPM=0 when the PPM unit 112 is connected to the blood pressure instrument 10. Assuming that PPM=0, the pulse status is set to invalid and not calculated (block 942), and a status check of PD is made (block 943). PD=0 represents reception of data pulse PULSE by the PPM unit 112 (note that reverse logic is employed), while PD=1 represents non-reception of pulse data. Upon reception of pulse data, the data counter is cleared (block 944), and a further check of PPM is made (block 945). So long as the PPM unit 112 is connected to the blood pressure instrument 10, a further check (via block 946) of PD is made. If PD has now transitioned to one, a flag check is made (block 948) in order to ensure that the same pulse (transition from zero to one) is not counted twice. If the flag is set, the data counter is incremented (block 949), thus counting a pulse, and the flag is reset and the timer incremented (block 950). If the flag is not set (block 948), the pulse is ignored (not counted), and block 950 is executed.

Block 951 constitutes a time check, and so long as a predetermined time has not been consumed in transferring pulse information, a loop to block 945 is executed. If the predetermined time has passed (block 951), further block 952 is executed, whereby if the data counted (in block 949) does not exceed 48, the routine is ended; conversely, if the data does equal or exceed 48, the pulse status is set to "valid and calculated," and the pulse transfer is completed, the data thus derived being converted to BCD for display in display unit 132 of PPM unit 112.

Bleed Valve and Solenoid

Figure 15:
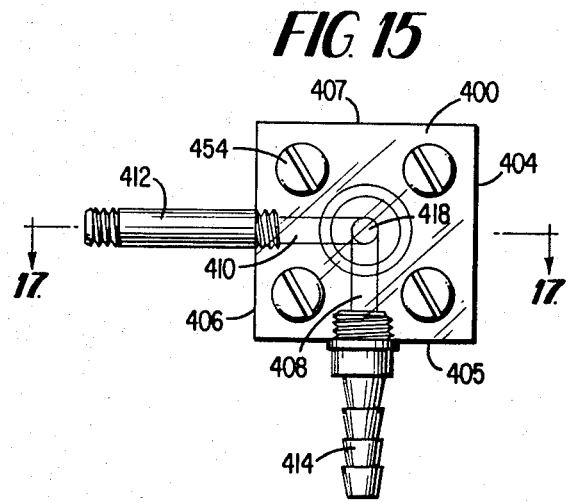
FIG. 15 is a top plan view of the solenoid valve assembly of FIG. 12.
Figure 16:
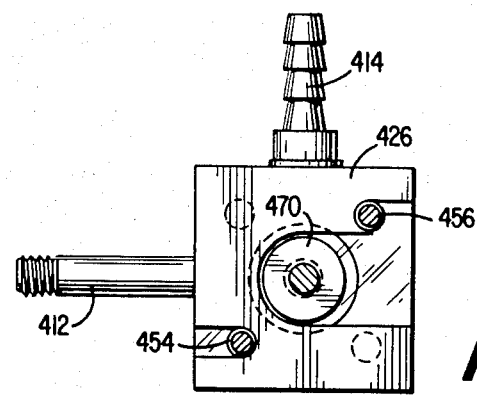
FIG. 16 is a sectional view taken along lines 16—16 of FIG. 14.

With reference to FIGS. 12 through 18 the details of the solenoid valve assembly 77, comprising the bleed valve 20 and the solenoid 78, will now be described. With reference to its orientation in FIG. 14, the bleed valve includes a generally rectangular shaped pressure block 400 which defines a top surface 402, a bottom surface 403, and four side walls 404 through 407. With reference to FIG. 15, a bore 408, in direct communication with a second bore 410, is defined within the housing so that one end of bore 408 terminates at surface 405 and one end of bore 410 terminates at surface 406.

A hollow nipple 412 has one end threadedly engaged in the pressure block so that the nipple communicates with the bore 410. The other end of nipple 412 is threadedly engaged with the pump housing 18 to provide a clear passageway for compressed air to pass from the pump housing 18 through the hollow nipple 412 into the bore 410. A hollow hose fitting 414 has one end threadedly engaged in the pressure block in direct communication with the bore 408. The other end of hose fitting 414 is secured to the flexible tubing 441 (shown in phantom in FIG. 13). In this way, compressed air entering bore 410 is free to flow through bore 408, hose fitting 414, flexible tubing 441 and into the pressure transducer 54.

Figure 17:
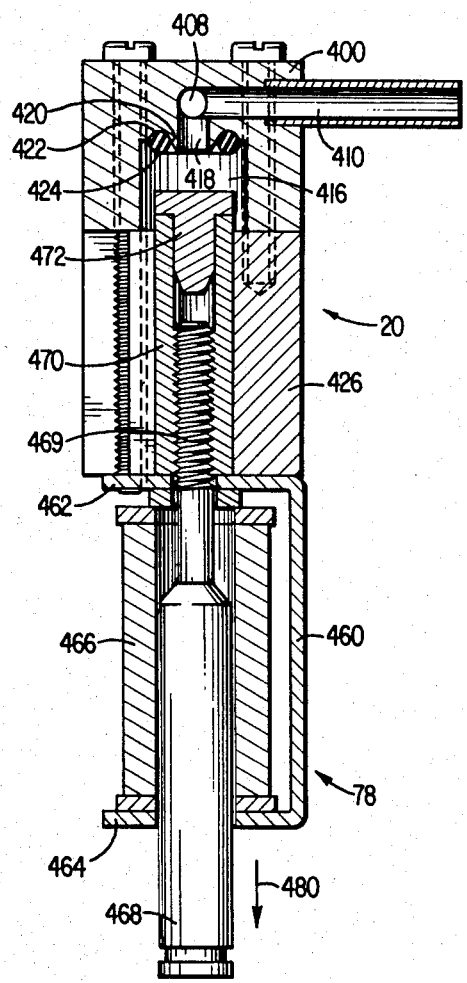
FIG. 17 is a sectional view taken along lines 17—17 of FIG. 15.

Defined within the pressure block is an additional bore 416 that extends from the bottom surface 403 to the point where bores 408 and 410 meet within the pressure block 400. With reference to FIG. 17, an orifice 418 provides a fluid passageway between bore 416 and bores 408 and 410. The outer surface of orifice 418 is marked by a tapered area 420 which circumscribes the orifice and is recessed into the pressure block 400 to define a ring shaped recess 422 for receiving a resilient O-ring 424.

An adaptor 426 is provided for connecting the pressure block 400 with the solenoid 78. The adaptor is generally a six-sided solid having a top surface 428, a bottom surface 430 and four side walls 431 through 434. The adaptor contains two evacuated portions 446 and 448 which each extend from the bottom surface 430 to the top surface 428 on opposite sides of the adaptor. These evacuated portions mate with bores 450 and 452 contained in the pressure block 400. In this way the pressure block with the adaptor disposed therebetween may be secured to the solenoid 78 through screws 454 and 456. In order to enhance the connection of the top surface 428 of the adaptor to the bottom surface 404 of the pressure block two additional screws 458 and 460 pass through bores within the pressue block 400 and are threadedly engaged within the adaptor 426.

The solenoid 78 generally comprises a U-shaped housing 460 having a top portion 462 and a bottom portion 464 between which is disposed coil 466. The coil slidably receives an armature 468 which terminates in a threaded portion 469 for threadedly engaging one end of a cylindrically shaped piston 470. The other end of the piston 470 is hollow to receive a resistant bumper 472.

The adaptor also contains an evacuated portion 474 which extends from the bottom surface 430 to the top surface 428 of the adaptor 426. When the pressure block 400, the adaptor 426, and the solenoid housing 460 are connected together by screws 454 and 456, a passageway is provided so that when the coil 466 is activated by a signal received on lines 76-1 and 76-2, the armature 468 moves within the solenoid and carries the bumper 472 atop the piston 472 through the adaptor and the bore 416 toward the O-ring 422.

Figure 18:
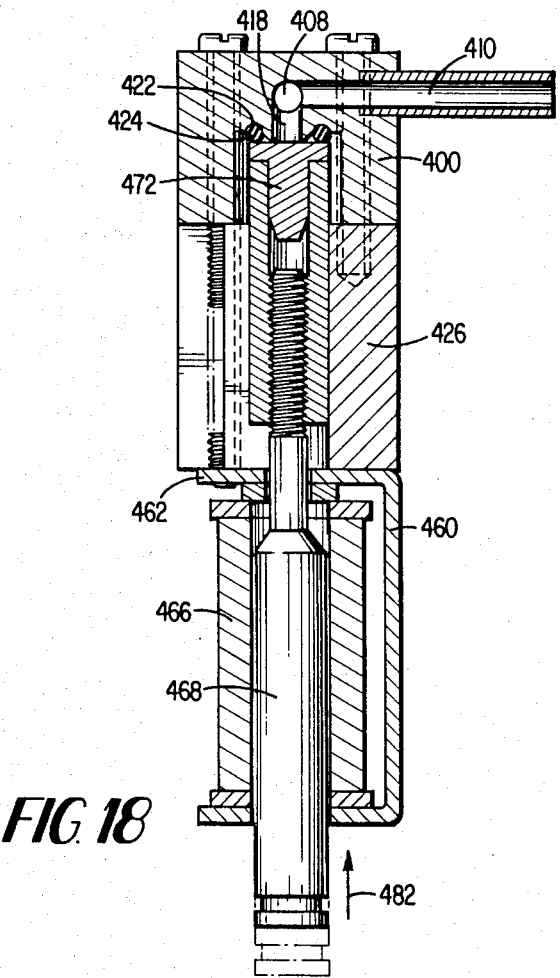
FIG. 18 is a view similar to that of FIG. 17.

With reference to FIGS. 17 and 18, in the absence of a current applied to the coil 466, the armature 468 travels under the force of gravity in the direction indicated by arrow 480 with the piston 470 and the bumper 472 following. This creates a condition within the bleed valve such that air entering the nipple 412 from the pressure chamber 18 passes through the orifice 418 into the bore 416 and is then free to pass into the evacuated portion 474 of the adaptor 426 and then into the atmosphere.

Upon application of a current to the coil 466, the armature 468 is driven in the direction of arrow 482, thus, in turn, driving the resilient bumper 472 up against the O-ring 422 to create a first seal which prevents any air from escaping from orifice 418 into bore 416. As the armature continues to move in the direction of arrow 482 the bumper 472 creates a second seal across the orifice 418. In this way a double seal is provided. Further, any air entering nipple 412 from the pressure chamber 18 passes through bores 410 and 408 into the pressure transducer 54 via hose fitting 414 and flexible hose 441.

Motor and Pump

Figure 19:
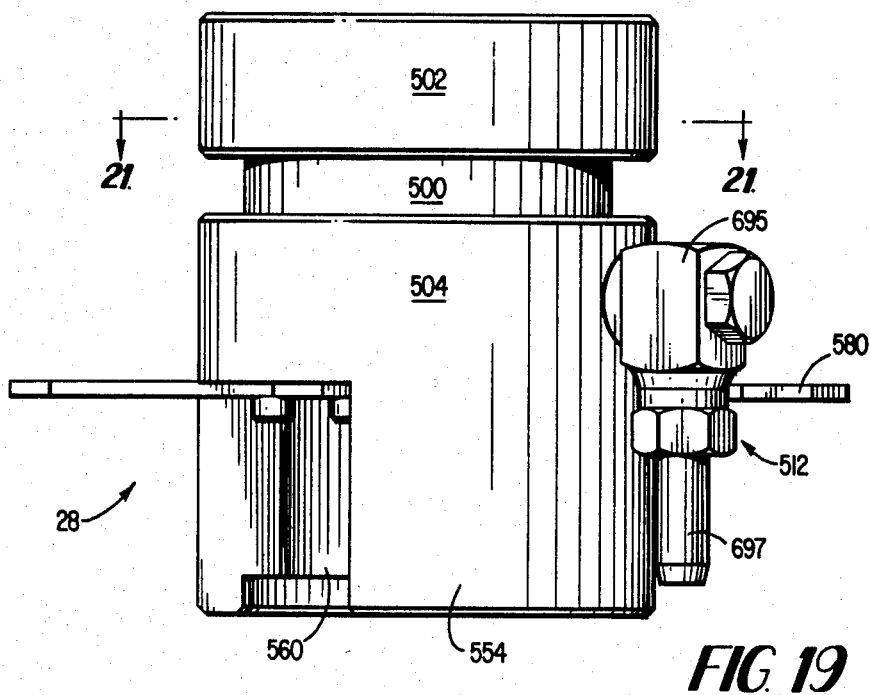
FIG. 19 is a side plan view of an embodiment of the pump used in the blood pressure system.
Figure 20:
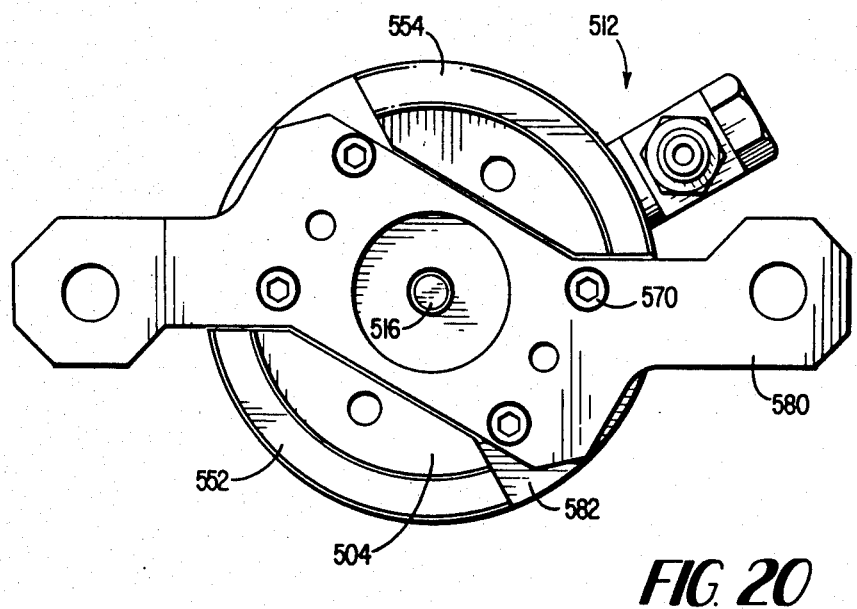
FIG. 20 is a bottom plan view of the pump.

With reference to FIGS. 19 through 23, and 28, the details of the motor 24 and the pump 28 will now be described. FIGS. 19 and 22, the pump 28 basically comprises a body portion 500, a top cover 502 and a base cover 504 which together define a chamber 506. A rotor 508 having a plurality of sliding vanes 510 is rotably mounted within the pump so that air from the atmosphere is drawn into the chamber 506 through fitting assembly 512, compressed by rotation of the rotor, and then expelled through bore 514 contained within the top cover 502. The shaft 516 of the rotor is secured by a conventional sub-miniature coupling 518 to the shaft 26 of a commercially available 12 volt D.C. motor 24.

With reference to FIGS. 21–24, the body 500 is generally cylindrically shaped to define a top surface 520, a bottom surface 522 and a side surface 524. A right circular bore 526 extends through the body portion from the top surface 520 to the bottom surface 522. The cylindrical axis A of the right circular bore 526 is off-set from, but parallel to, the cylindrical axis B of the body part. A dowel 528 extends transversely through the body 500 to provide a means for registering the orientation of the top cover 502 and the base cover 504 with respect to the body part 500.

The top cover 502 comprises an outer sleeve 530. A cylindrically shaped plug 534 is pressed fit into a mating area defined within the sleeve 530. The plug 534, which is made of a suitable polyimide such as Vespel, manufactured by E.I. Dupont, contains an aperture 536 which receives one end of the dowel 528 in order to properly orient the body 500 against the plug 534 when the top cover 502 is placed against the top surface 520 of the body 500. The top cover 502 is secured to the body 500 by a suitable fastening means such as screws 538 which are received in threaded apertures 540 defined in the body 500.

A bore 542 communicates with a channel 544 on the inner surface of the top cover 502 to provide a passage way for outlet 514 for compressed air contained within the chamber 506.

The base cover 504 comprises a sleeve 550 which terminates in two opposed leg portions 552 and 554. A cylindrically shaped Vespel plug 556 is pressed fit into a mating area defined within the sleeve 550. The sleeve 550 of the base cover 504 contains a recess 566 which is shaped to receive the bottom portion of the body. The bottom surface 522 of the body 500 is held in intimate contact with the top surface 568 of the plug 556 by suitable fastening means such as screws 570 which engage with threaded bores 540 in the body 500. The inner surface 568 of the base cover 504 contains a bore 572 which receives a portion of the dowel 528 to properly orient the base cover with respect to the body 500.

A channel 574 is defined in the inner surface 568 of the base cover 504. This channel communicates with a bore 576 in the plug 556 and the sleeve 550 to provide a passageway for air from the atmosphere to enter within the chamber 506.

A mounting bracket 580 lies against a surface 582 defined between the two legs of the base cover and is secured thereto by the screws 570. The mounting bracket 580 is used to mount the pump 28 within the pressure chamber 18 in a manner to be described hereinafter.

As shown in FIGS. 21, 22 and 24, the securing together of the body 500 with the top cover 502 and the base cover 504 define the right circular bore 506. Positioned within the bore is the rotor 508 which defines a top surface 584, a bottom surface 586 and a side surface 590. The shaft 516 extends through the cylindrical axis of the rotor 508. One shaft end 592 is received within a bore 594 of the top cover, while the other end 596 is received within bore 598 of the base cover. Since the bores 594 and 598 are within the Vespel plugs 534 and 556, respectively, an excellent bearing surface is supplied for the rotational mounting of the rotor 508 within the chamber 506.

The rotor 508 contains a plurality of spaced slots 600 each for receiving a vane 510. Each vane is capable of sliding within the slot with which it is associated. Thus, as shown in FIG. 21, as the rotor 508 rotates, the rotation of the rotor forces the vanes 510 outward and away from the axis of rotation of the rotor. Thus, a number of air chambers 610 are created as the individual vanes press up against the side wall 612 of the chamber 506. The number of chambers 610, which in this case is 12, is chosen to reduce air pressure pulsations that could interfere with the detection of K-sounds in the blood pressure system.

As the rotor rotates, the chambers 610 change size. In this way air entering through the inlet enters one of the larger chambers 610′. As the rotor continues to rotate, chamber 610′ gradually decreases in size until it assumes a volume 610″. The outlet of the pump receives the air in chamber 610″ which has been compressed through the rotation of the rotor 508.

Figure 23A:
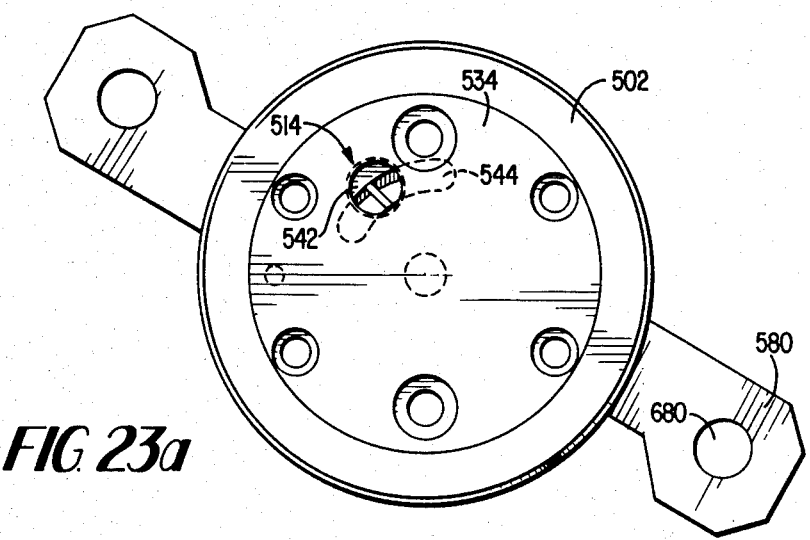
FIG. 23a is a top plan view of the pump.
Figure 23B:
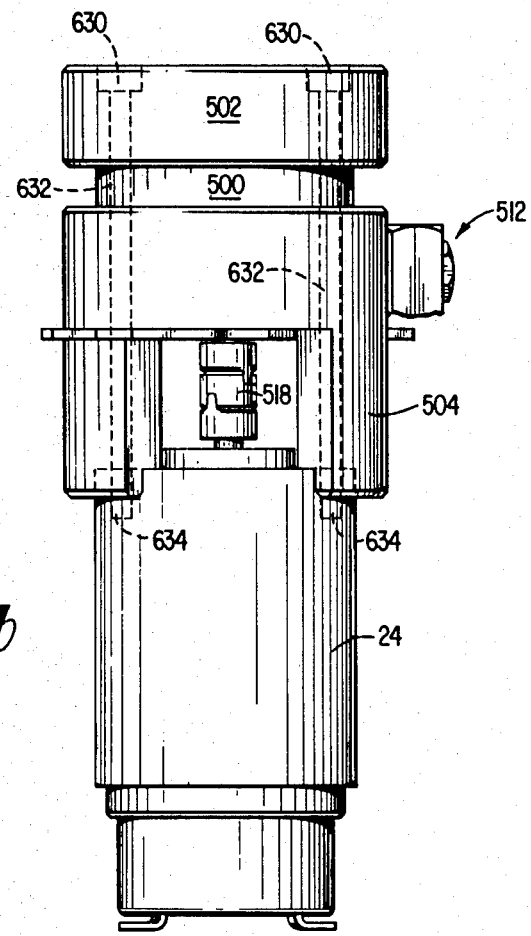
FIG. 23b is a plane view of a motor mounted to the pump.

The motor 24 is typically a 12 volt DC motor having a no load speed of approximately 5,035 rpm, plus or minus 10%. A conventional sub-miniature coupling 518 secures the motor shaft 26 to the shaft of the rotor 516. As best shown in FIGS. 23b and 24, the motor 24 is secured to the under side of the pump through suitable fastening means such as the pair of screws 630 (in phantom) which are received in opposed bores 632 which extend through top cover 504, the body 500 and the base cover 502. The screws are placed in these bores and received in threaded bores 634 defined in the motor 24.

Pump Housing

With reference to FIGS. 25–36 the pump housing will now be described in detail. The pump housing generally designated as 650, is a generally rectangular shaped structure which, through a vertical mid wall 652, is divided into a pressure chamber 18 and a compartment 654. As shown in FIG. 31, the pressure chamber 18 houses the pump 28 and the motor 24. The compartment 654 houses the bleed valve 20 and the solenoid 78. The cells 656 constituting the battery 94 are also contained within the compartment and are held therein by a bracket 658 which is received in a pair of slots 660 (FIG. 26) contained within opposing side walls 662 and 664 of the compartment 654.

Figure 25:
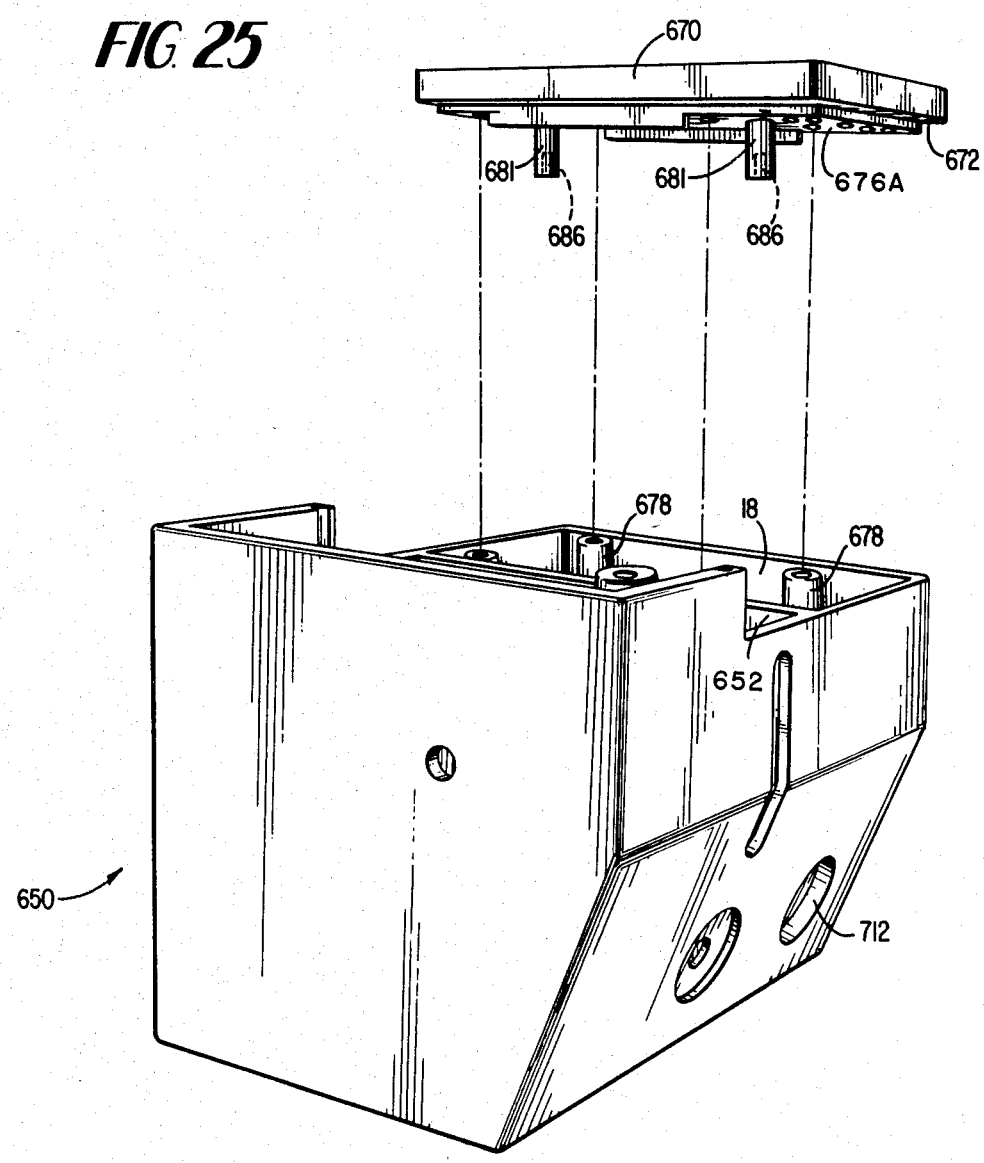
FIG. 25 is an exploded plan view of an embodiment of the pump housing used in the blood pressure system.
Figure 26:
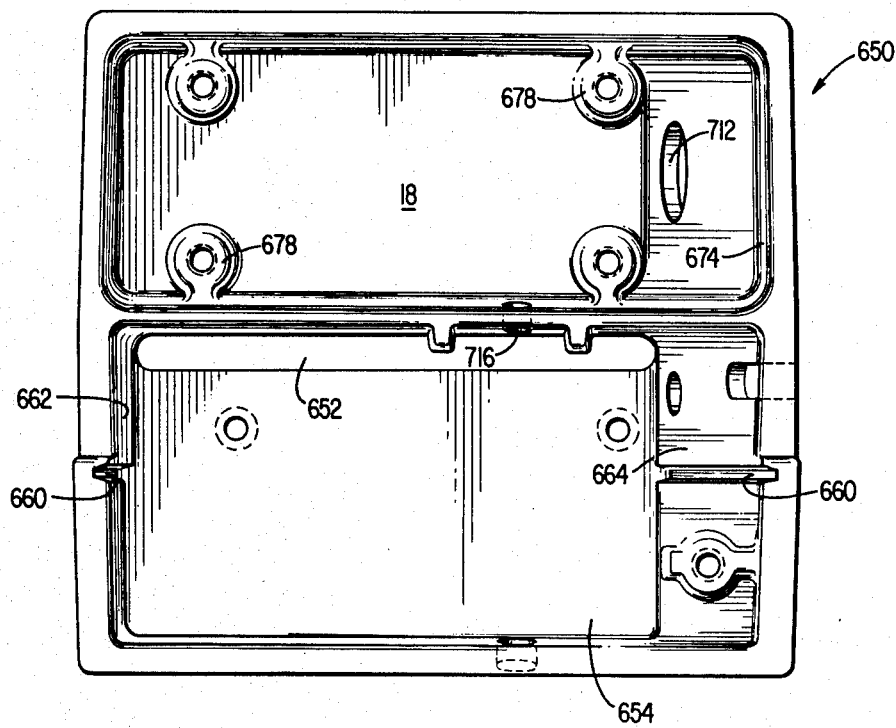
FIG. 26 is a top plan view of the pump housing with the cover removed.
Figure 27:
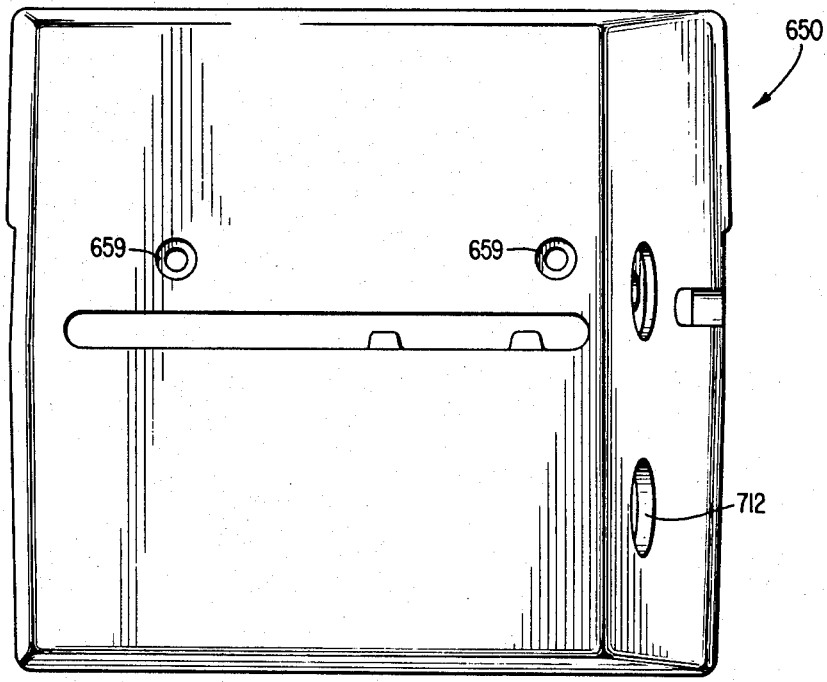
FIG. 27 is a bottom plan view of the pump housing.
Figure 35:
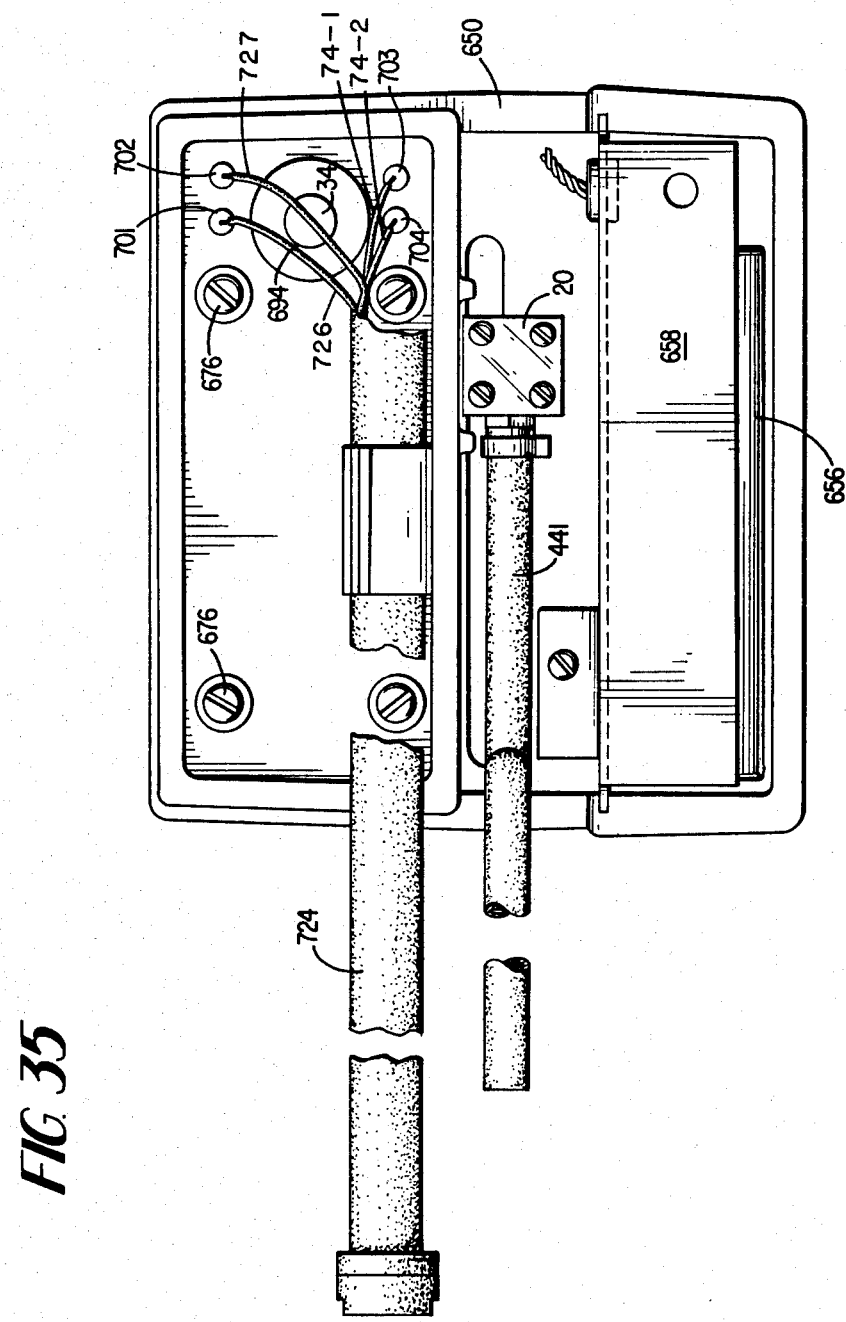
FIG. 35 is a top plan view of the pump housing with the cover, the solenoid valve assembly, and the battery pack mounted in place.

With reference to FIGS. 25, 26 and 35, the pressure chamber 18 is open at one side in a generally rectangular configuration. This open side receives a cover 670 which contains a rim 672 which mates with a rim 674 in the open area of the pressure chamber. The cover 670 is secured to the top of the pressue chamber by suitable fastening means such as screws 676 which are received in threaded extensions 678 provided around the rim 674.

Figure 28:
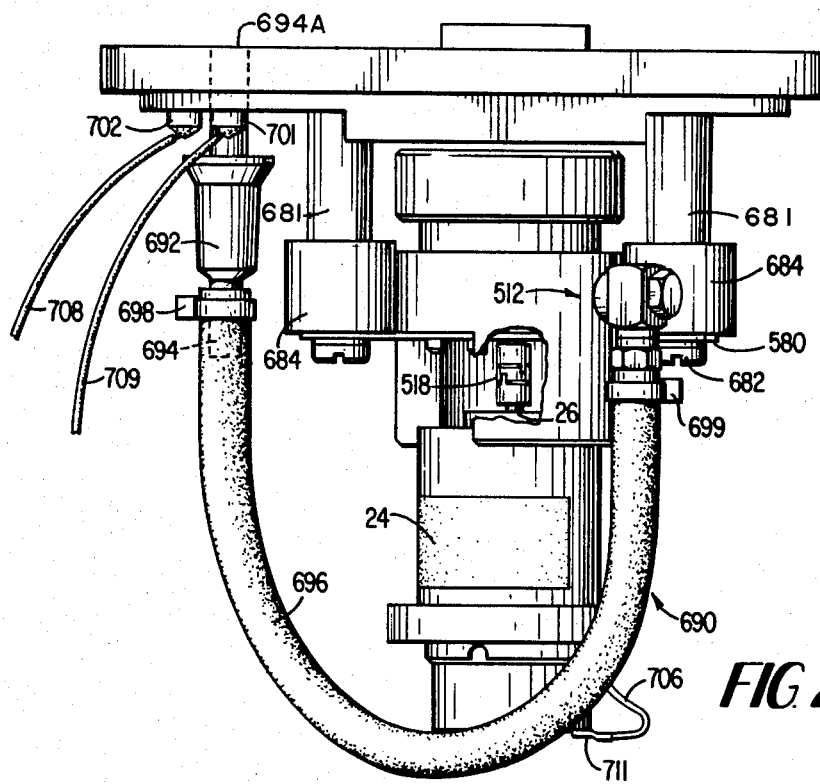
FIG. 28 is a side plan view of the motor and pump assembly mounted to the cover of the pump housing.
Figure 29:
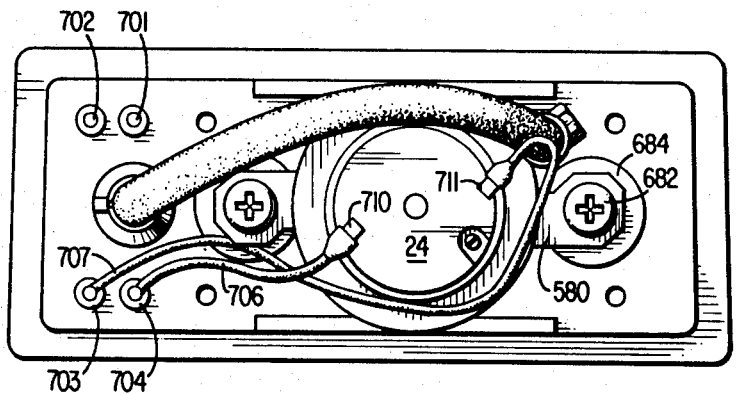
FIG. 29 is a bottom plan view of that shown in FIG. 28.
Figure 32:
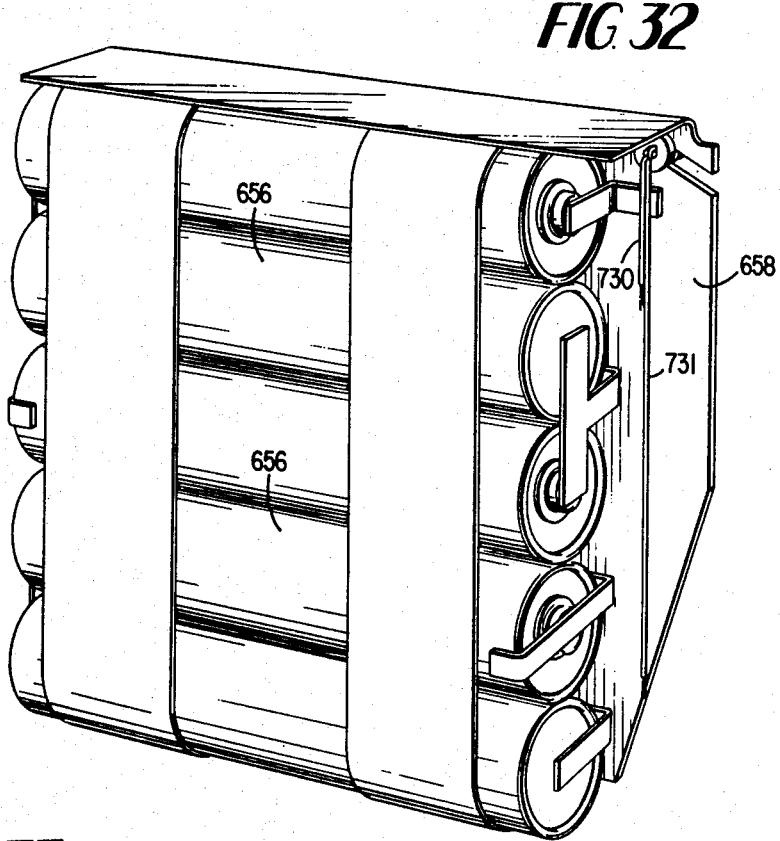
FIG. 32 is a plan view showing the battery mounted on the battery mounting bracket.
Figure 33:
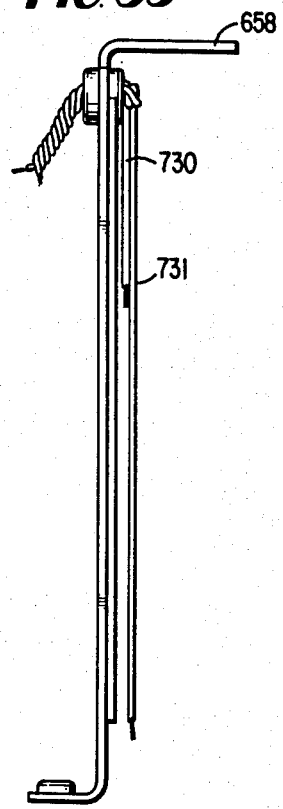
FIG. 33 is a side plan view of the battery mounting bracket.
Figure 34:
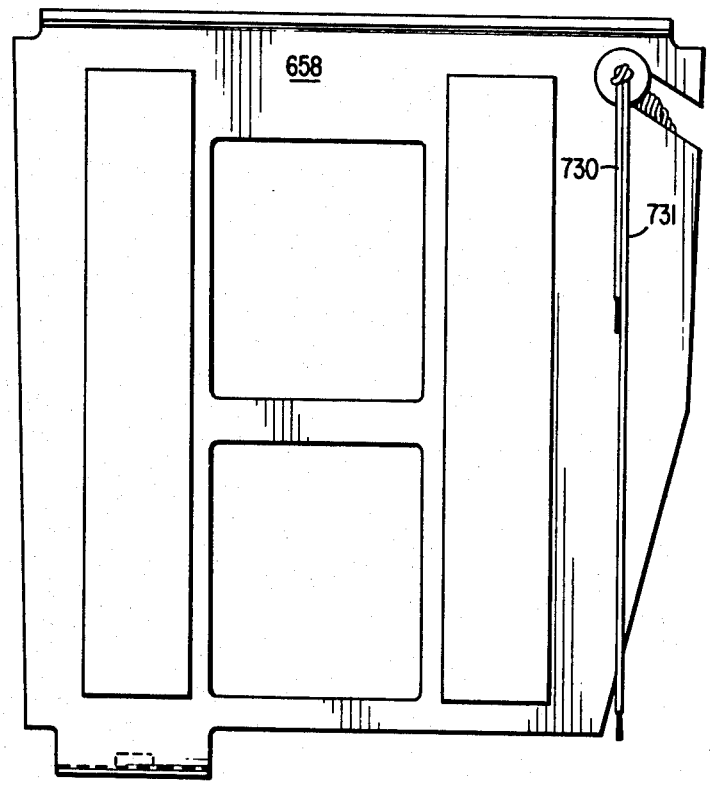
FIG. 34 is a plan view of the battery mounting bracket with the battery removed.

As shown in FIGS. 25, 28 and 29, the components housed within the pressure chamber 18 are mounted to the underside 676A of the cover 670. The underside 676A contains two stanchions 681 which are positioned to mate with the apertures 680 contained in the mounting bracket 580 of the motor pump assembly. A screw 682 passes through each of the mounting apertures 680 and then through resilient vibration mount 684 to be readily engaged in the bores 686 provided in each stanchion 681. When mounted, the pump motor assembly 690 is oriented so that the top cover 504 is closest to the inner surface 676A of the cover 670. The fitting assembly 512, which comprises an elbow-fitting 695 and a hose fitting 697 is readily engaged in the aperture 576 contained on the outer wall of the base cover (see also FIGS. 19, 21 and 22).

A check valve 692 is mounted within a bore 694A provided in the cover 670. The check valve 692 contains an extended tubular portion 694 which receives one end of a flexible tube 696. The tube is held in place about the tubular member 694 by a tie wrap 698. The other end of the tube 696 is fitted about the hose fitting 697 and is held in place by a second tie wrap 699. In this way a passageway is provided for air in the atmosphere to be drawn into the chamber 506 of the pump 28. Air entering the chamber passes through an air filter 34, the check valve 692, the flexible tubing 696, and then finally through the fitting assembly 512 into the chamber 506. With reference to FIGS. 29 and 35, four feedthroughs 701 through 704 are mounted on the cover 670. The feedthroughs maintain the airtight seal between the chamber and the outside atmosphere. The portions of the feedthroughs 703 and 704 extending into the pressure chamber 18 receive a pair of wires 706 and 707 which are secured to the terminals 710 and 711 of the motor 24. The portion of the feedthroughs 701 and 702 extending into the pressure chamber 18 receive a pair of wires 708 and 709 which constitute the microphone leads of the blood pressure instrument.

As best seen in FIGS. 25, 30 and 31, an aperture 712 in a side wall 714 of the pressure chamber 18 receives a conventional air-tight fitting 713 for mounting a flexible tubing 22 which in turn is connected to the blood pressure cuff 16. The wires 708 and 709, constituting the microphone leads, are contained within the flexible tubing 22 and run throughout the full length of the tubing for connection to the microphone contained within the blood pressure cuff.

With reference to FIG. 31, the pump housing 650 is shown in its position of intended use. Mounted within the compartment 654 is the bleed valve 20 and the solenoid 78. The bleed valve is mounted by passing the nipple 412 through an aperture 716 provided in the vertical side wall 652 and then securing it with hex nut 718. A pressure block gasket 720 is interposed between the bleed valve 20 and the side wall 652 to ensure that no air excapes from the pressure chamber 18.

As can be seen, armature 468 of the solenoid assembly 78 is free to drop under the force of gravity in the absence a current being applied to the coil 466. A pair of leads 722 and 723, connected to the coil 466, are run into the cable tubing 724 (FIG. 35) and then routed within the instrument to leads 76-1 and 76-2 of the inflate/deflate controller 72 as shown in FIG. 4. The cable 724 also contains a pair of leads 74-1 and 74-2 which are connected to the external portion of the feedthroughs 703 and 704. An additional pair of leads 726 and 727, connected to the external portions of the feedthroughs 701 and 702, are fed through the cable 724 to the amplifer 46-1 of the sound sensor 150 as shown in FIG. 2.

The cells 656 constituting the battery 94 are mounted within the remainder of the compartment 654 through a battery bracket 658. The bracket is held in place by a suitable fastening such as a pair of screws 657, which fit within bores 659 in the pump housing. A pair of leads 730 and 731 are connected to the plus and minus terminals of the battery pack and then to the regulated power supply 86. (See FIG. 1)

Although the present invention has been shown and described in terms of a specific preferred embodiment, it will be appreciated by those skilled in the art that changes or modifications are possible which do not depart from the inventive concepts described and taught herein. Such changes and modifications are deemed to fall within the purview of these inventive concepts.

What is claimed is:

1. A blood pressure system for automatically measuring systolic and diastolic pressure in a patient, said system comprising:
   blood pressure cuff means, adapted for attachment about a limb of the patient and capable of being inflated to occlude the artery of the limb during an inflation cycle and capable of being deflated during a deflation cycle;
   pressure chamber means in fluid communication with said cuff means so that, at any given time, the pressure within said chamber is substantially the same as the pressure within said cuff means;
   transducer means for producing an electrical signal indicative of the actual pressure within said chamber means;
   error means receiving the electrical signal from said transducer means for producing an error signal indicative of the difference between the actual rate of change of pressure within said chamber and a desired rate of change of pressure within said chamber;
   pressure increasing means responsive to said error signal during said inflation cycle, said pressure increasing means comprising means for variably duty cycle modulating said error signal to produce a control signal and means responsive to said control signal for increasing the pressure within said chamber thereby inflating said cuff; and
   pressure decreasing means responsive to said error signal during said deflation cycle, said pressure decreasing means comprising means for variably duty cycle modulating said error signal to produce a control signal and means responsive to said control signal for decreasing the pressure within said chamber thereby deflating said cuff.

2. A blood pressure system for automatically measuring systolic and diastolic pressure in a patient, said system comprising:
   (A) blood pressure cuff means, adapted for attachment about a limb of the patient and capable of being inflated and deflated;
   (B) a first servo control loop for increasing the pressure within said cuff means at a constant rate during an inflation cycle, said first loop comprising,
      (a) transducer means for producing an electrical signal indicative of the actual pressure within said cuff means,
      (b) error means receiving the electrical signal from said transducer means for producing an error signal indicative of the difference between the actual rate of change of pressure within said cuff means and a desired rate of change of pressure within said cuff means, and
      (c) pressure increasing means responsive to said error signal during said inflation cycle, said pressure increasing means comprising means for variably duty cycle modulating said error signal to produce a control signal and means responsive to said control signal for increasing the pressure within said cuff means; and
   (C) a second servo control loop for decreasing the pressure within said cuff means at a constant rate during a deflation cycle, said second loop comprising,
      (a) transducer means for producing an electrical signal indicative of the actual pressure within said cuff means, (b) error means receiving the electrical signal from said transducer means for producing an error signal indicative of the difference between the actual rate of change of pressure within said cuff means and a desired rate of change of pressure within said cuff means, and (c) pressure decreasing means responsive to said error signal during said deflation cycle, said pressure decreasing means comprising means for variably duty cycle modulating said error signal to produce a control signal and means responsive to said control signal for decreasing the pressure within said cuff means.

3. The blood pressure system of claim 2, wherein said first servo control loop transducer means and said second servo control loop transducer means are a single pressure transducer.

4. The blood pressure system of claim 1, wherein said first servo control loop error means and said second servo control loop error means are a single error means.

5. A blood pressure system for automatically measuring systolic and diastolic pressure in a patient, said system comprising:

(A) blood pressure cuff means, adapted for attachment about a limb of a patient and capable of being inflated to occlude the artery of the limb during an inflation cycle and capable of being deflated during a deflation cycle;

(B) pressure chamber means in fluid communication with said cuff means so that, at any given time, the pressure within said chamber is substantially the same as the pressure within said cuff means;

(C) a first servo control loop for increasing the pressure within said chamber at a constant rate during said inflation cycle, said first loop comprising, (a) transducer means for producing an electrical signal indicative of the actual pressure within said chamber means, (b) error means receiving the electrical signal from said transducer means for producing an error signal indicative of the difference between the actual rate of change of pressure within said chamber means and a desired rate of change of pressure within said chamber means, (c) modulating means for variably duty cycle modulating said error signal to produce a control signal, and (d) means responsive to said control signal for increasing the pressure within said chamber; and (D) a second servo control loop for decreasing the pressure within said chamber at a constant rate during said deflation cycle, said second loop comprising, (a) transducer means for producing an electrical signal indicative of the actual pressure within said chamber means, (b) error means receiving the electrical signal from said transducer means for producing an error signal indicative of the difference between the actual rate of change of pressure within said chamber means and a desired rate of change of pressure within said chamber means, (c) modulating means for variably duty cycle modulating said error signal to produce a control signal, and (d) means responsive to said control signal for decreasing the pressure within said chamber.

6. The blood pressure system of claim 5, wherein said first servo control loop transducer means and said second servo control loop transducer means are a single pressure transducer.

7. The blood pressure system of claim 5, wherein said first servo control loop error means and said second servo control loop error means are a single error means.

* * * * *